US008906870B2

(12) United States Patent
Thum et al.

(10) Patent No.: US 8,906,870 B2
(45) Date of Patent: *Dec. 9, 2014

(54) MICRORNA (MIRNA) FOR THE DIAGNOSIS AND TREATMENT OF HEART DISEASES

(75) Inventors: Thomas Thum, Wuerzburg (DE); Johann Bauersachs, Wuerzburg (DE)

(73) Assignee: Julius-Maximilians-Universitaet Wuerzberg, Wuerzburg (DE)

( * ) Notice: Subject to any disclaimer, the term of this patent is extended or adjusted under 35 U.S.C. 154(b) by 884 days.

This patent is subject to a terminal disclaimer.

(21) Appl. No.: 12/445,042

(22) PCT Filed: Oct. 9, 2007

(86) PCT No.: PCT/EP2007/008772
§ 371 (c)(1),
(2), (4) Date: Jun. 8, 2009

(87) PCT Pub. No.: WO2008/043521
PCT Pub. Date: Apr. 17, 2008

(65) Prior Publication Data
US 2010/0010073 A1    Jan. 14, 2010

(30) Foreign Application Priority Data
Oct. 9, 2006    (EP) .................................... 06090187

(51) Int. Cl.
C12N 15/11        (2006.01)
C12Q 1/68         (2006.01)
C12N 15/113       (2010.01)
C07H 21/04        (2006.01)

(52) U.S. Cl.
CPC ........ *C12Q 1/6883* (2013.01); *C12Q 2600/178* (2013.01); *C12N 2310/11* (2013.01); *C12Q 2600/136* (2013.01); *C12N 2310/14* (2013.01); *C12Q 2600/158* (2013.01); *C12N 2330/10* (2013.01); *C12N 15/113* (2013.01)
USPC ........................................ 514/44 A; 536/24.5

(58) Field of Classification Search
None
See application file for complete search history.

(56) References Cited

U.S. PATENT DOCUMENTS

| 2005/0261218 | A1* | 11/2005 | Esau et al. ........................ 514/44 |
| 2006/0019286 | A1  | 1/2006  | Horvitz et al. |
| 2006/0185027 | A1  | 8/2006  | Bartel et al. |
| 2007/0049547 | A1* | 3/2007  | Esau et al. ........................ 514/44 |
| 2009/0192102 | A1* | 7/2009  | Bader et al. ....................... 514/44 |
| 2009/0306181 | A1* | 12/2009 | Ikeda et al. ................... 514/44 A |

FOREIGN PATENT DOCUMENTS

WO   WO 2004/076622   9/2004
WO   WO 2006/027776   3/2006

OTHER PUBLICATIONS van Rooij et al., A signature pattern of stress-responsive microRNAs that can evoke cardiac hypertrophy and heart failure, 2006, PNAS, vol. 103, pp. 18255-18260.*
Si et al., miR-21-mediated tumor growth, 2007, Oncogene, vol. 26, pp. 2799-2803.*
Chan et al., MicroRNA-21 is an antiapoptotic factor in human glioblastoma cells, 2005, Cancer Research, vol. 65, pp. 6029-6033.*
Lim et al., Reversal of cardiac hypertrophy in transgenic disease models by calcineurin inhibition, 2000, Journal of Molecular and Cellular Cardiology, vol. 32, pp. 697-709.*
Lagos-Quintana et al., Identification of tissue-specific microRNAs from mouse, 2002, Current Biology, vol. 12, pp. 735-739.*
Patent Cooperation Treaty, "International Search Report", PCT/EP2007/008772, 11 pages, Jun. 19, 2008.
Patent Cooperation Treaty, "International Preliminary Report on Patentability—Written Opinion of the International Searching Authority (English translation)", PCT/EP2007/008772, 16 pages including cover sheet, Jun. 23, 2009.
Buitrago M., et al. "The transcriptional repressor Nab1 is a specific regulator of pathological cardiac hypertrophy", Nature Medicine, 11, 837-44, 2005.
Burkard N., et al. "Targeted proteolysis sustains calcineurin activation", Circulation, 111:1046-53, 2005.
Chen J-F., et al. "The role of microRNA-1 and micro-RNA-133 in skeletal muscle proliferation and differentiation", Nature Genetics 38, 228-233 (including 16 pages of supplementary figures and tables), 2006.
Chien K., "Molecular medicine: microRNAs and the tell-tale heart", Nature, 447, 389-390, 2007.
Harfe B. D., "MicroRNAs in vertebrate development", Curr Opin Genet Dev, 15, 410-415, 2005.
Heineke J., et al., "Regulation of cardiac hypertrophy by intracellular signalling pathways", Nature rev. mol. cell biol., 7, 589-600, 2006.
Hornstein E., et al., "The microRNA miR-196 acts upstream of Hoxb8 and Shh in limb development", Nature, 438, 671-674, 2005.
Huber W., et al., "Variance stabilization applied to microarray data calibration and to the quantification of differential expression", Bioinformatics, 18, 96-104, 2002.
Hunter J. J. and Chien K. R., "Molecular and cellular biology of cardiac hypertrophy and failure", (Philadelphia: W. B. Saunders), 211-250, 1999.

(Continued)

*Primary Examiner* — Dana Shin
(74) *Attorney, Agent, or Firm* — Viksnins Harris & Paddys PLLP

(57) ABSTRACT

The invention relates to microRNAs (miRNAs) for the diagnosis, prophylaxis and/or treatment of heart diseases. It relates in particular to SEQ ID No: 1 to SEQ ID No: 29 for the diagnosis, prophylaxis and/or treatment of heart diseases. In addition, the invention relates to the use of these sequences to produce a medicament for heart diseases and for the diagnosis thereof. Also encompassed are a method for the diagnosis of a heart disease, a kit and an expression vector comprising these sequences, a cell which contains the expression vector, and also a method for modulating a heart disease and a method for screening a pharmaceutically active compound for the treatment and/or prophylaxis of a heart disease.

6 Claims, 13 Drawing Sheets

(56) References Cited

OTHER PUBLICATIONS

Hutvagner G. and Zamore, P. D., "A microRNA in a multiple-turnover RNAi enzyme complex", Science, 297, 2056-2060, 2002.

Krutzfeldt J., et al., "Silencing of microRNAs in vivo with 'antagomirs", Nature, 438, 685-689, 2005.

Lu, J., et al., "MicroRNA expression profiles classify human cancers", Nature, 435, 834-838, 2005.

Massie B. M. and Shah N. B., "Evolving trends in the epidemiologic factors of heart failure: rationale for preventive strategies and comprehensive disease management", Am Heart J 133, 703-712, 1997.

Meister G., et al., "Identification of Novel Argonaute-Associated Proteins", Curr Biol. 15, 2149-2155, 2005.

Pfeffer M. A. and Braunwald E., "Ventricular remodeling after myocardial infarction", Experimental observations and clinical implications, Circulation 81, 1161-1172, 1990.

Sayed D., et al., "MicroRNAs play an essential role in the development of cardiac hypertrophy", 100, 416-424, 2007.

Smyth G.K., "Linear models and empirical Bayes methods for assessing differential expression in Microarray experiments", Statistical Applications in Molecular Biology, 3, 1-25, (including abstract page and errata sheet), 2004.

Thum T. and Borlak J., "Reprogramming of gene expression in cultured cardiomyocytes and in explanted hearts by the myosin ATPase inhibitor butanedione monoxime", Transplantation, 71, 543-52, 2001.

Thum T., et al., "Bone marrow molecular alterations after myocardial infarction: Impact on endothelial progenitor cells", Cardiovasc Res, 70, 50-60, 2006.

Thum T., et al., "MicroRNAs in the human heart: a clue to fetal gene reprogramming in heart failure", Circulation, 116, 258-67 (including correction page), 2007.

Zhao Y., et al., "Serum response factor regulates a muscle-specific microRNA that targets Hand2 during cardiogenesis", Nature 436, 214-220, 2005.

U.S. Appl. No. 60/848,212, filed Apr. 10, 2008, Ikeda et al.

\* cited by examiner

D

E

Cy3-antagomir and DAPI in vivo

Only DAPI in vivo

F

G

MICRORNA (MIRNA) FOR THE DIAGNOSIS AND TREATMENT OF HEART DISEASES

FIELD OF THE INVENTION

The invention relates to microRNAs (miRNAs) for the diagnosis, prophylaxis and/or treatment of heart diseases.

The invention relates in particular to SEQ ID No: 1 to SEQ ID No: 29 for the diagnosis, prophylaxis and/or treatment of heart diseases. In addition, the invention relates to the use of these sequences to produce a medicament for heart diseases and for the diagnosis thereof. Also encompassed by the invention are a method for the diagnosis of a heart disease, a kit and an expression vector comprising these sequences, a cell which contains the expression vector, and also a method for modulating a heart disease and a method for screening a pharmaceutically active compound for the treatment and/or prophylaxis of a heart disease.

BACKGROUND OF THE INVENTION miRNAs

MicroRNAs (miRNAs) are small, non-coding RNA molecules which are able to regulate gene expression posttranscriptionally through degradation of the messenger RNA. The total number of different miRNAs is estimated to be approximately 300-500. miRNAs thus constitute approximately 1% of the human genome. miRNAs have been discovered in various species and appear to be highly conserved.

Although the target genes (or targets) and thus the biological functions of miRNAs have to date largely not been able to be identified, it is estimated that miRNAs regulate up to 30% of the genes of the human genome.

Firstly, miRNA genes are transcribed by RNA polymerase II into long primary miRNAs (pri-miRNAs). The further processing of these pri-miRNAs takes place in a step-by-step manner and in various compartments. Pri-miRNAs are firstly transformed in the cell nucleus by the RNase III enzyme Drosha into precursor miRNAs (pre-miRNAs) comprising approximately 70-80 nucleotides. Drosha forms a microprocessor complex with the RNA-binding protein DGCR8. Pre-miRNA hairpins are conveyed out of the cell nucleus by the protein exportin-5 and Ran-GTP as cofactor. In the cytoplasm, the pre-miRNA is processed by the RNase II enzyme Dicer to form duplex-miRNAs comprising approximately 22 nucleotides. Dicer interacts in this case with the double-stranded RNA-binding protein TRBP. The miRNA duplex molecules are then unwound, so that mature miRNA is obtained. This mature miRNA is then incorporated in a ribonucleoprotein complex (miRNP), which is very similar to the RNA-induced silencing complex (RISC), the effector molecule of interfering RNA (RNAi) (Hutvagner and Zamore, 2002).

In this form, miRNAs can lead to a downregulation of the respective target gene via two different mechanisms: a) translational inhibition or b) target mRNA cleavage. The choice of mechanism depends on the degree of complementarity between miRNA and the target gene in combination with a so-called Argonaute Protein (Meister et al., 2005). In the case of almost perfect complementarity, a cleavage of the target gene takes place with subsequent RNA degradation, whereas a translational inhibition takes place in the case of only partial complementarity (Hutvagner and Zamore, 2002). The precise mechanism of translational inhibition is not yet known (cf. FIG. 1, which shows the prior art).

While it has already been possible to explain some mechanisms for controlling differentiation processes by miRNAs (Harfe, 2005; Hornstein et al., 2005), the regulation of physiological functions by miRNAs is still largely unknown.

The large number of miRNAs and the regulated target genes thereof forecast an important role of miRNA in the onset and progression of a wide range of diseases. For example, most of the miRNAs identified in different tumor samples are downregulated (Lu et al., 2005).

The literature has already dealt once with the regulation of heart-specific development. Zhao et al. were able to show that certain muscle-specific miRNAs play a critical role in regulating heart development (Zhao et al., 2005). For instance, the miRNAs miR1-1 and miR1-2 are particularly expressed in cardiac precursor cells. A target of miR-1 is the cardiac transcription factor Hand2, which in turn controls the expansion of the ventricle during development. It is highly likely that miR-1 counteracts an excessively fast and exaggerated heart development (Zhao et al., 2005).

A further possible role of miRNA in the control of rebuilding processes after myocardial infarction or other heart diseases, such as e.g. hypertrophy or myocarditis, appears probable, but information about this is not yet available.

Possible Importance of miRNA in the Pathogenesis and Healing Processes of Various Cardiac Diseases Improper healing after myocardial infarction with scar formation and subsequent reduced left-ventricular pump function is the most frequent cause of heart failure in Western industrialized countries (Massie and Shah, 1997). The rates of hospitalization due to heart failure have almost doubled in the European countries in the last 10-15 years. The prognosis in the case of heart failure is not good and is almost as bad as for many malignant tumors. Due to the increasingly high life expectancy of the population, the incidence and prevalence of heart failure will increase further. In the new millennium too, therefore, heart failure will be one of the central challenges for the health service.

The term "cardiac remodeling" (Pfeffer and Braunwald, 1990) describes the processes of rebuilding the heart under pathophysiological conditions after myocardial infarction or in the case of other diseases (e.g. myocarditis) which may lead to heart failure. While in the early phase after myocardial infarction there is necrosis of the ischemic myocardium with subsequent scar formation, in the case of a myocardium not directly affected by infarction there are changes over the long term which must initially be regarded as healing and adaptation processes. The thinning and dilatation of the infarcted myocardial wall may in the early stages (days to weeks) of the post-infarct phase lead to infarct expansion; late remodeling (months to years) is caused by a structural reconfiguration of the surviving myocardium, which is characterized by myocyte hypertrophy, interstitial fibrosis, apoptotic cardiomyocyte loss and also dilatation and deformation of the heart chamber.

The essential characteristics of these structural changes include cellular hypertrophy of the remaining myocardium, reduced capillarization and also a progressive myocardial fibrosis (Pfeffer and Braunwald, 1990). These initial rebuilding processes are a compensatory response, but ultimately the changes lead to a progressive left-ventricular dilatation and restriction of the left-ventricular pump function, which are characterized by high mortality.

The process of cardiac remodeling also comprises molecular, cellular and interstitial changes. It is not only cardiomyocytes that are affected (phenotype change with hypertrophy and reduced contractility, necrosis, apoptosis), but also in particular the extracellular matrix and a change in the inflammatory milieu. Cardiac remodeling is influenced by hemodynamic changes, neurohormonal activation, inflammatory cytokines and a plurality of other processes. Chronic heart failure, and also acute myocardial infarction, are characterized by increased plasma levels of pro-inflammatory cytokines (inter alia tumor necrosis factor-alpha, interleukin-1-beta, -2 and -6) and also the soluble receptors thereof. In the failing myocardium, inflammatory cytokines are expressed. Besides the known negative inotropic effect of these cytokines, pronounced effects on the myocyte phenotype and the extracellular matrix in the case of chronic heart failure should in the longer term be of particular pathophysiological importance. For a current overview of cellular and molecular mechanisms in heart failure, reference is made to the more in-depth literature (Hunter, 1999).

In clinical studies, it was possible to demonstrate a significant improvement in prognosis under treatment using medicaments (beta-blockers, ACE inhibitors, aldosterone antagonists). Nevertheless, heart failure is and remains one of the most frequent causes of death in industrialized countries.

The search for and development of new forms of treatment to improve cardiac healing processes has become one of the greatest challenges in modern cardiology. The use of miRNAs offers new possibilities for an optimized treatment and/or diagnosis of heart diseases.

The object of the present invention is therefore to specify various miRNA sequences which are suitable for the diagnosis, prophylaxis and/or treatment of heart diseases.

SUMMARY OF THE INVENTION

The invention relates to SEQ ID No: 1 to SEQ ID No: 29 for the diagnosis, prophylaxis and/or treatment of heart diseases. In addition, the invention relates to the use of these sequences to produce a medicament for heart diseases and for the diagnosis thereof. The invention also relates to a method for the diagnosis of a heart disease, a kit and an expression vector comprising these sequences, a cell which contains the expression vector, and also a method for modulating a heart disease and a method for screening a pharmaceutically active compound for the treatment and/or prophylaxis of a heart disease.

The invention will be described in more detail below with reference to the appended figures and on the basis of various embodiments.

DETAILED DESCRIPTION OF THE INVENTION AND PREFERRED EMBODIMENTS

Figure 1:
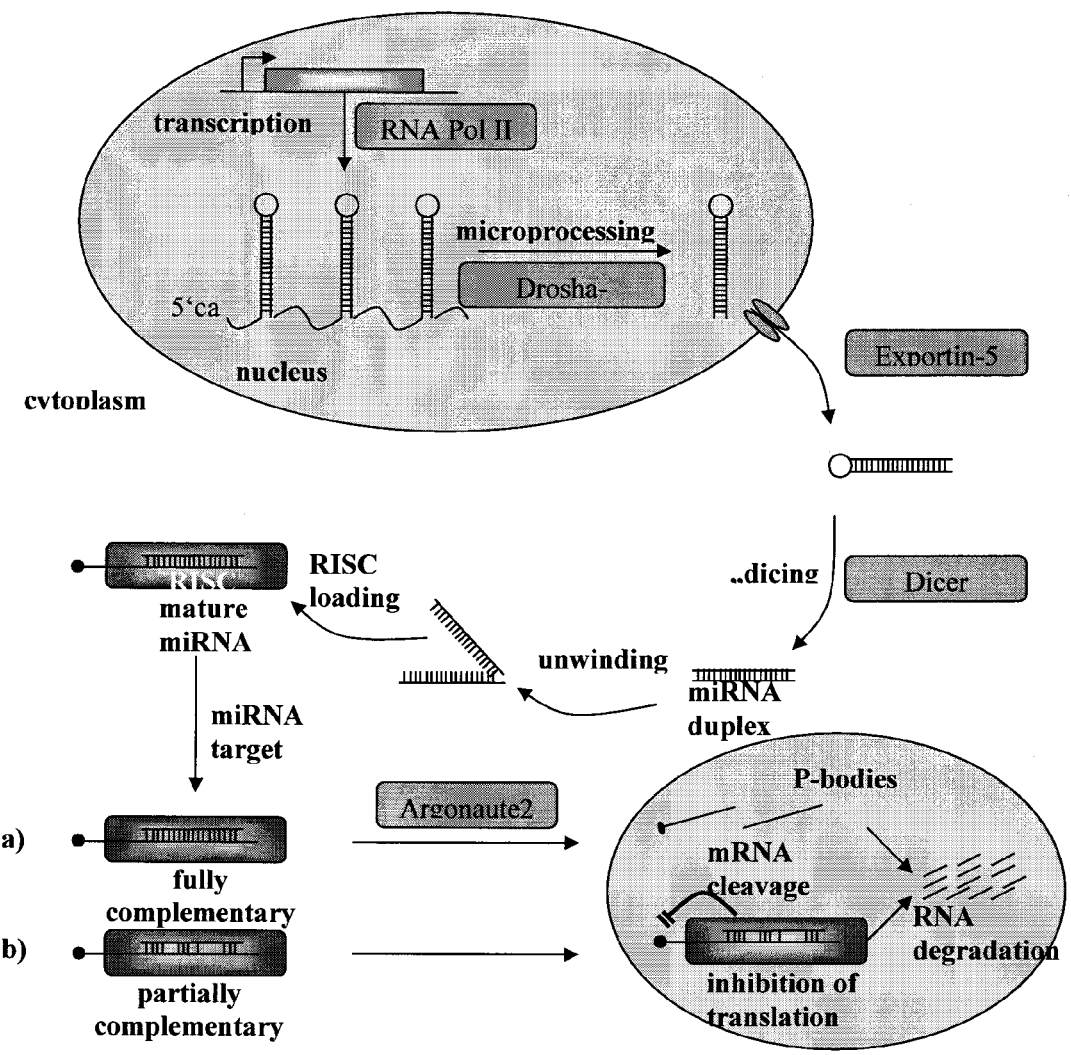
FIG. 1 represents the prior art and shows the maturing of miRNA and the inhibition processes of mRNA.

The present invention relates to miRNA sequences, in particular SEQ ID No: 1 to SEQ ID No: 29, for the diagnosis, prophylaxis and/or treatment of heart diseases. The sequences are shown in the sequence listing and are summarized in Table 2.

Furthermore, SEQ ID No: 1 to SEQ ID No: 29 can be used to produce a medicament for the prophylaxis and/or treatment of heart diseases.

Moreover, SEQ ID No: 1 to SEQ ID No: 29 can be used for the diagnosis of heart diseases.

In one particularly preferred embodiment, the heart disease is myocardial infarction, heart failure, in particular chronic heart failure and/or cardiac hypertrophy.

A further subject matter of the invention is a method for the diagnosis of a heart disease, wherein the method comprises the steps:
(a) providing a sample from an individual suspected of suffering from a heart disease;
(b) measuring the expression level of at least one sequence selected from SEQ ID No: 1 to SEQ ID No: 29 in the sample;
wherein an increased or reduced expression level of at least one sequence selected from SEQ ID No: 1 to SEQ ID No: 29 compared to a control sample indicates a heart disease or a prevalence or predisposition to a heart disease.

A further embodiment relates in particular to the use of the sequence SEQ ID No: 5 (miR-134), SEQ ID No: 10 (miR- 212), SEQ ID No: 11 (miR-214), SEQ ID No: 14 (miR-21), SEQ ID No: 20 (miR-182) and/or SEQ ID No: 24 (miR-290).

Particular preference is given in particular to miR-21 (SEQ ID No: 14). This miRNA is upregulated approximately 3.3-fold in human heart failure and early after cardiac hypertrophy (aortic banding 3 days) approximately 3.0-fold in mice.

Preference is also given to miR-212 (SEQ ID No: 10). This miRNA is upregulated approximately 5.6-fold in human heart failure and after chronic myocardial infarction approximately 2.4-fold in rats.

Preference is furthermore given to miR-214 (SEQ ID No: 11). This miRNA is upregulated slightly in human heart failure approximately 1.2-fold and clearly early and late after cardiac hypertrophy (aortic banding 3 and 21 days) approximately 1.5-fold and respectively approximately 2.1-fold in mice and also after chronic myocardial infarction approximately 2.6-fold and after pharmacological cardiac hypertrophy induction in vitro approximately 1.5-fold.

Finally, preference is given to miR-134 (SEQ ID No: 5). This miRNA is upregulated slightly in human heart failure approximately 1.2-fold and clearly late after cardiac hypertrophy (aortic banding 21 days) approximately 1.7-fold in mice and also after chronic myocardial infarction (3.3-fold) in rats.

All upregulated miRNAs can be normalized via miRNA inhibitors in vitro and in vivo in terms of their expression as a treatment. Furthermore, they can be used as diagnostic markers.

In one alternative embodiment, preference is given to miR-182 (SEQ ID No: 20). This miRNA is downregulated in human heart failure (−1.3-fold) and clearly early and late after cardiac hypertrophy (aortic banding 3 and 21 days) (−1.8-fold and respectively −2.2-fold) in mice and also after chronic myocardial infarction (−4.0-fold) in rats.

Preference is also given to miR-290 (SEQ ID No: 24). This miRNA is downregulated in human heart failure (−1.4-fold) and early after cardiac hypertrophy (aortic banding 3 days) (−1.6-fold) in mice and also after chronic myocardial infarction (−1.4-fold) in rats.

These reduced or downregulated miRNAs can be normalized via exogenously added miRNAs. Furthermore, medicaments can be developed which normalize the expression of the miRNAs. Moreover, they can optionally also be used together with the upregulated miRNAs as diagnostic markers.

A further subject matter of the invention concerns a kit comprising at least one sequence selected from SEQ ID No: 1 to SEQ ID No: 29 for the diagnosis of heart diseases.

Also encompassed by the invention is an expression vector comprising at least one sequence selected from SEQ ID No: 1 to SEQ ID No: 29.

In one particular embodiment, the invention also encompasses a cell comprising at least one expression vector.

A further aspect of the present invention relates to a method for modulating a heart disease, which comprises modulating the expression or activity of at least one sequence selected from SEQ ID No: 1 to SEQ ID No: 29 in a cell.

Yet another subject matter of the invention relates to a method for screening a pharmaceutically active compound for the treatment and/or prophylaxis of a heart disease, wherein the method comprises the steps:
(a) providing a cell according to the invention,
(b) bringing a candidate for a pharmaceutically active compound into contact with the cell,
(c) determining the effect of the candidate on the expression of a sequence selected from SEQ ID No: 1 to SEQ ID No: 29, wherein a change in the expression of at least one sequence selected from SEQ ID No: 1 to SEQ ID No: 29 indicates a pharmaceutically active compound.

It should furthermore be noted that all the features mentioned in the application documents and in particular in the dependent claims, despite the fact that they may formally refer back to one or more specific claims, are also covered by independent protection individually or in any combination with one another.

The invention will be described in more detail in the following examples and results, which are given only by way of example and are not to be understood in a limiting manner.

EXAMPLES AND RESULTS

1. MicroRNA Analyses after Myocardial Infarction

Figure 2:
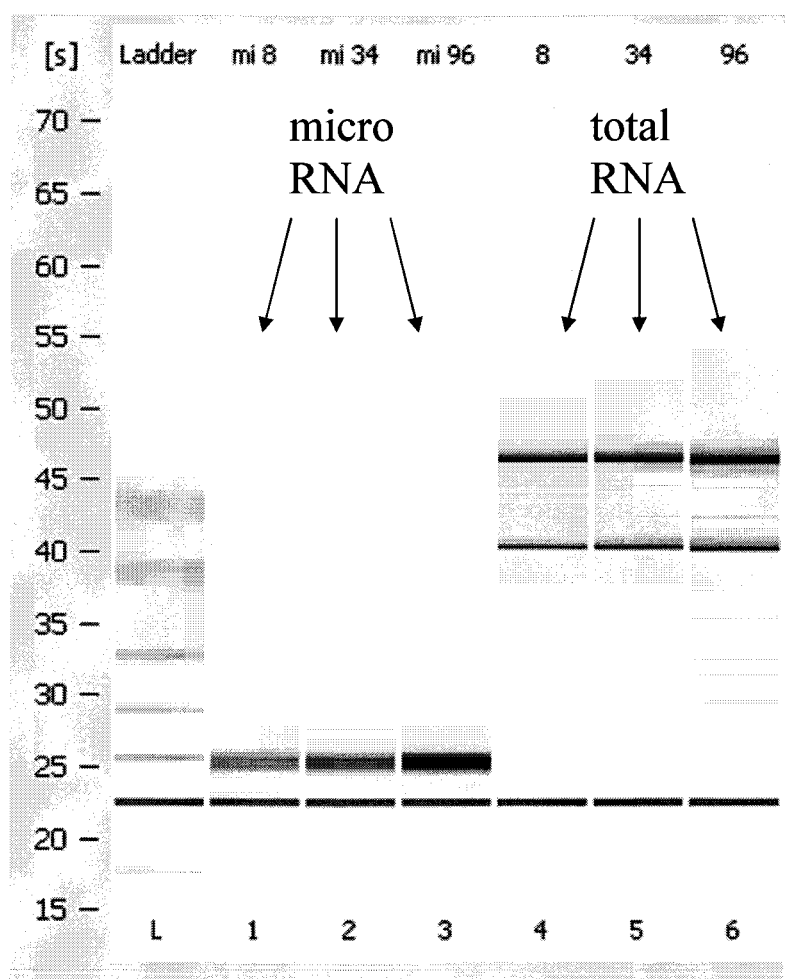
FIG. 2 shows isolated miRNA and total RNA by capillary electrophoresis.

All the necessary procedures for the isolation and microarray-based detection of >300 different miRNAs from myocardial tissue were established in the laboratory. For instance, by adding a further step of separation by means of gel electrophoresis, it was possible to optimize miRNA isolation to such an extent that good labeling was possible for the subsequent hybridization and detection of miRNAs on a spotted special miRNA microarray (in cooperation with the IZKF Microarray Facility, Dr. S. Kneitz) (see FIG. 2 and FIG. 3). By comparing healthy myocardium with chronically infarcted myocardium from rats, it was possible to identify numerous deregulated miRNAs which represent interesting target structures for subsequent research approaches and also interesting diagnostic markers.

The inventors were thus already able, using microarray-based techniques, to identify a number of miRNAs which are highly expressed in the heart. Numerous differentially expressed miRNAs in the chronically infarcted myocardial tissue indicate an important role in cardiac remodeling.

The following miRNAs are induced after myocardial infarction (>1.2 times that of the sham-operated animals). Mean values from n=3 animals per group are given:
miR211 (SEQ ID No: 9), miR16-1, miR137, miR195, miR199a*-1, miR199a-2, miR145, miR96, miR101-1, miR368, miR193, miR297-1, miR125b-1, miR1-2, let7f-1, miR295, miR199a-1, miR198, miR291-3p, miR99a, miR210, miR293, miR350, miR409, miR339, miR103-1, miR129-2, miR190, miR325, miR367, miR291-5p, let7d*, miR19a, miR369, miR300, miR199a*-2, miR98, miR221, miR292-3p, miR126, miR136, miR17-3p, miR128a (SEQ ID No: 4), miR15b (SEQ ID No: 1), miR151 (SEQ ID No: 7), miR328 (SEQ ID No: 12), miR126* (SEQ ID No: 3), miR23a (SEQ ID No: 2), miR212 (SEQ ID No: 10), miR149 (SEQ ID No: 6), miR206 (SEQ ID No: 8), miR214 (SEQ ID No: 11), miR371 (SEQ ID No: 13), miR134 (SEQ ID No: 5).

The following miRNAs are repressed after myocardial infarction (<80% of that of the sham-operated animals). Mean values from n=3 animals per group are given:
miR106b, miR182 (SEQ ID No: 17), miR296 (SEQ ID No: 18), miR122a (SEQ ID No: 19), miR30a-3p (SEQ ID No: 20), miR372, miR182*, miR298, miR9-1, miR155, miR99b, miR147, miR197, miR189, miR154, miR376b, miR219-1, miR202; miR370, miR341, miR27a, let7e, miR302c*; miR188, miR200b, miR215, miR142-3p, miR153-1, miR345, miR34a, miR21, miR148a, miR146, miR290, let7i, miR106a, miR217, let7g, miR183, miR200a, miR133a-1, miR7-1, miR22, miR9-1*, miR93, miR144, miR34c, miR220, miR141, miR130b.

For selected miRNA sequences, the respective SEQ ID No: is given in brackets.

Figure 3:
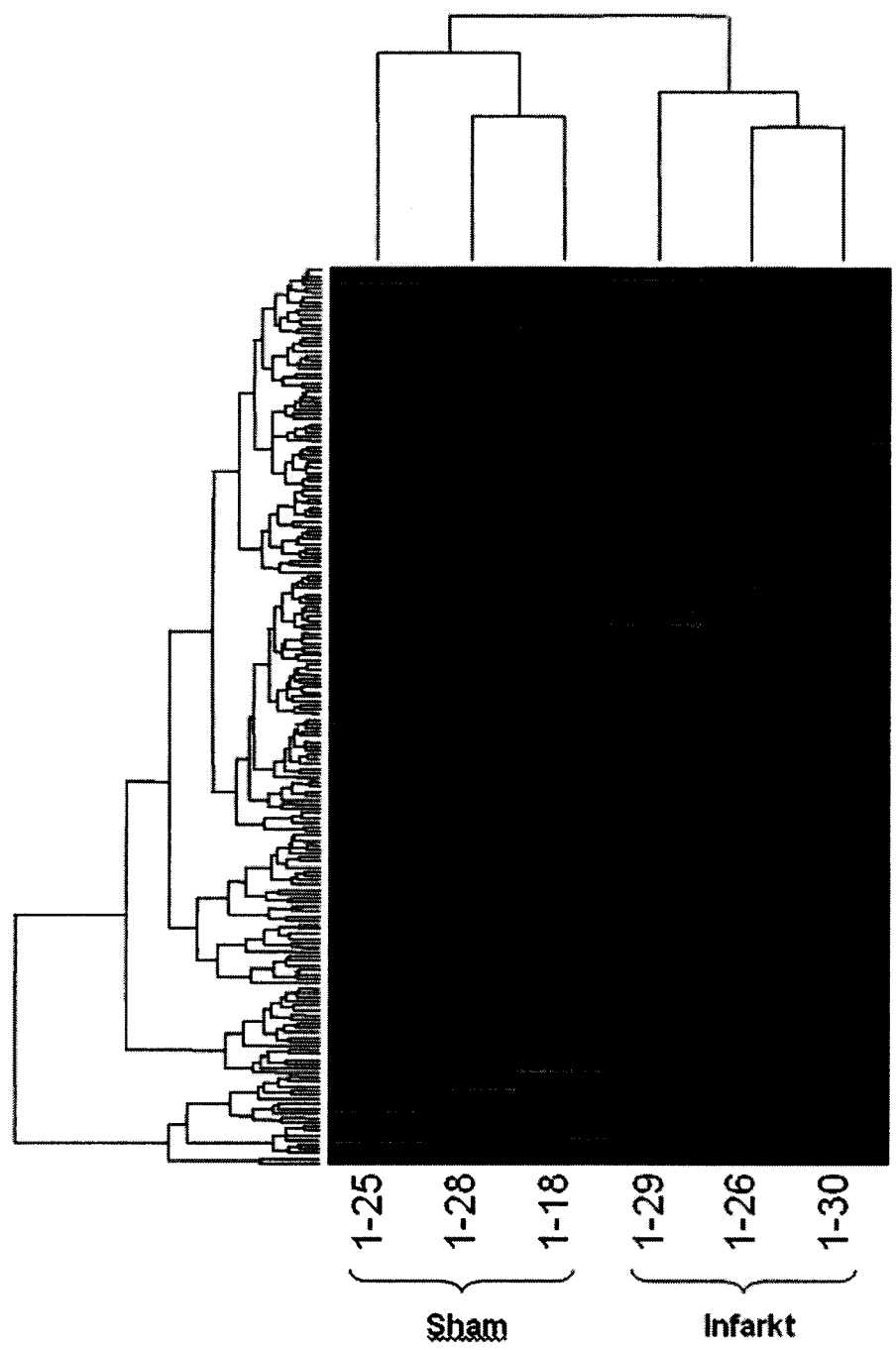
FIG. 3 shows a hierarchical cluster analysis of deregulated miRNAs; it is possible to see the significant differences in chronically infarcted myocardial tissue (infarct; n=3) and myocardial tissue of sham-operated rats (sham; n=3).

A hierarchical cluster analysis according to Eisen (online at rana.lbl.gov) likewise showed the significant differences in chronically infarcted myocardial tissue (infarct; n=3) and myocardial tissue from sham-operated rats (sham, n=3) (see FIG. 3). This bioinformatic analysis method searches for differences and similarities between the different groups studied.

By searching in databases (online at microma.sanger.ac.uk), it was already possible to identify theoretical target genes of the deregulated miRNAs. A selection is given in Table 1.

TABLE 1 miRNAs upregulated after myocardial infarction and the target genes thereof, which play an important role in myocardial infarction/heart failure

| miRNA | Target gene |
|---|---|
| miR15b (SEQ ID No: 1) | Carnitine O-palmitoyltransferase II (fatty acid oxidation) |
| | Cyclin A2 |
| | G1/S-specific cyclin E1 |
| | Myosin-binding protein C, cardiac type (cardiac MyBP-C) |
| | Superoxide dismutase [Cu—Zn] |
| | Fibroblast growth factor 6 |
| miR23a (SEQ ID No: 2) | L-lactate dehydrogenase B chain |
| | Hypoxia-inducible factor 1 alpha inhibitor |
| | Retinoid X receptor gamma |
| | Cyclin H |
| | Thioredoxin |
| | Cyclin L1 (cyclin L) |
| miRNA126* (SEQ ID No: 3) | Vascular cell adhesion protein 1 precursor (V-CAM 1) |
| | Vascular endothelial growth factor A precursor (VEGF-A) |
| | Histone H2B |
| miRNA128a (SEQ ID No: 4) | Vascular endothelial growth factor C precursor |
| | Thioredoxin reductase 2 |
| | 6-phosphofructokinase, muscle type |
| | Troponin I, cardiac muscle (cardiac troponin I) |
| | Myosin heavy chain, cardiac muscle alpha isoform (MyHC-alpha) |
| | Somatotropin precursor (growth hormone) |
| | Thioredoxin reductase 2 |
| | Metalloproteinase inhibitor 1 precursor (TIMP-1) |
| miRNA134 (SEQ ID No: 5) | Calreticulin |
| | Cytochrome C oxidase polypeptide Va, mitochondrial precursor |
| | Peroxiredoxin 1 (EC 1.11.1.15) (thioredoxin peroxidase 2) |
| miRNA149 (SEQ ID No: 6) | Carnitine O-acetyltransferase |
| | Voltage-gated potassium channel subfamily D member 3 |
| | Growth arrest and DNA-damage-inducible 45 beta |
| | Tropomyosin 1 alpha chain (alpha-tropomyosin) |
| miRNA151 (SEQ ID No: 7) | Myosin-binding protein C, cardiac type (cardiac MyBP-C) (cardiac muscle isoform) |
| | Calcium-activated potassium channel beta subunit 4 |
| | Heparin-binding growth factor precursor (acidic fibroblast growth factor) (aFGF). |
| miRNA206 (SEQ ID No: 8) | Cytochrome b5 |
| | Superoxide dismutase [Cu—Zn] |
| | Cyclin H |
| | Angiopoietin-like 2 |
| miRNA211 (SEQ ID No: 9) | Bone morphogenetic protein 10 precursor (BMP-10) |
| | Intermediate-conductance calcium-activated potassium channel protein 4 (SK4) (KCa4) |
| | Nitrogen oxide synthase, brain m(EC 1.14.13.39) (NOS type I) (neuronal NOS) (N-NOS) |
| | Voltage-gated potassium channel subfamily H member 7 (voltage-gated potassium channel subunit Kv11.3) |
| | Nestin |
| | Matrix metalloproteinase-9 precursor (EC 3.4.24.35) (MMP-9) |
| | Atrial natriuretic peptide receptor B precursor (ANP-B) |
| | Myogenic factor 6 |
| | Vascular cell adhesion protein 1 precursor (V-CAM 1) (CD106 antigen) |
| miRNA212 (SEQ ID No: 10) | Myosin-5B (myosin Vb) (myosin heavy chain myr 6) |
| | Calcium-activated potassium channel beta subunit 4 |
| | Isocitrate dehydrogenase [NAD] subunit beta, mitochondrial precursor |
| | Transcription factor E2F5 (E2F-5) |
| | Mitochondrial carnitine/acylcarnitine carrier protein |
| | Vascular cell adhesion protein 1 precursor (V-CAM 1) |
| | Ryanodine receptor type 1 |
| | Metalloproteinase inhibitor 1 precursor (TIMP-1) |
| | Voltage-gated potassium channel subfamily A member 6 (Kv1.6) |

TABLE 1-continued miRNAs upregulated after myocardial infarction and the target genes thereof, which play an important role in myocardial infarction/heart failure

| miRNA | Target gene |
|---|---|
| miRNA214 (SEQ ID No: 11) | Carnitine O-acetyltransferase<br>Creatine kinase M-type<br>Myosin-binding protein H (MyBP-H)<br>Metalloproteinase inhibitor 4 precursor (TIMP-4)<br>Myosin XVIIIa<br>Superoxide dismutase [Cu—Zn]<br>Myosin light polypeptide 6 (Myosin light chain alkali 3) (myosin light chain 3)<br>Cardiac troponin C |
| miRNA328 (SEQ ID No: 12) | Calcium-activated potassium channel beta subunit 4<br>Myosin-binding protein H<br>Calcium/calmodulin-dependent protein kinase kinase 1 (EC 2.7.1.37)<br>Sodium- and chlorine-dependent creatine transporter 1 (CT1) (creatine transporter 1)<br>Voltage-gated potassium channel subfamily D member 3 (Kv4.3)<br>IGF-II mRNA-binding protein 1<br>Nestin<br>Fructose-1,6-bisphosphatase 2<br>Myoglobin |
| miRNA371 (SEQ ID No: 13) | Somatotropin precursor (growth hormone)<br>Creatine kinase B-type (EC 2.7.3.2) (creatine kinase, B chain) (B-CK) |

Individual strongly regulated miRNAs can be modulated by an upregulation (by liposomal transfection of the specific miRNA) or downregulation (by liposomal transfection of specific miRNA inhibitors (anti-miRs®, Ambion, UK or Antagomirs, Alnylam, Kulmbach, Germany)) of the corresponding miRNA by application after myocardial infarction. Alternatively, other types of transfection may also be used (e.g. viral or by nucleofection, or electroporation). Due to the large number of target genes of individual miRNAs, whole gene networks are thus re-normalized with regard to their expression after myocardial infarction, and an improved cardiac function is restored.

2. Methods of MiRNA Expression Screening miRNA Expression Analyses

Frozen heart tissue or cultured cardiomyocytes were comminuted using liquid nitrogen. From these, total RNA including small RNAs was isolated (mirVana™ miRNA isolation kit; Ambion, USA). The total RNA was isolated separately and the purified miRNAs were prepared using the FlashPAGE fractionation system (Ambion, USA). Capillary electrophoresis (Bioanalyzer 2100; Agilent, Germany) was used to assess the quality of the total RNA and the purity of the miRNA.

MicroRNA obtained from 10 µg of total RNA was labeled with the dye Cy3 (Molecular Probes, USA) using the mirVana™ miRNA labeling kit (Ambion, USA) according to the manufacturer's instructions. Each target was hybridized in a separate array.

Microarrays containing up to 384 miRNAs (mirVana miRNA probe set, Ambion) were spotted 4 times each in the inventors' laboratory onto SCHOTT Nexterion® Slide E microarray slides. The oligonucleotide probes had a length of 42-46 nt and consisted of an 18-24 nt segment which targeted a specific known miRNA originating from humans, mice or rats.

A complete list of the probes used, including the sequence information in the probe set, is available on the world-wide-web at ambion.com/techlib/resources/-miRNA_array/index.html. The preparation of the slide, the miRNA purification, the enrichment and labeling were carried out according to the instructions given in the Ambion handbook for mirVana™ (on the world-wide-web at ambion.com/techlib/prot/). The data acquisition was carried out using the ScanAlyze software (M. Eisen, LBNL, CA, USA).

Data Analysis of the Arrays

The miRNA array data analyses were carried out using the R-package from the Bioconductor project (on the world-wide-web at bioconductor.org). The resulting signal intensities were normalized by variance stabilization (Huber et al., 2002). The quality of all the data sets was tested, and a statistical analysis was carried out in order to evaluate differentially expressed genes using the Limma (Linear Models for Microarray Analysis) package. The key function of the Limma package is an implementation of Smyth's empirical Bayes linear modeling approach and can even be used for the stable analysis of even smaller sample sizes (Smyth, 2004).

Methods to Predict the miRNA Target (See Table 1)

The miRNA database miRBase (online at microrna.sanger.ac.uk) was used to identify possible miRNA targets. The miRanda algorithm was used to screen all the available miRNA sequences of a given genome for the 3' UTR sequences of this genome. The algorithm uses dynamic programming to search for the maximum local complementarity corresponding to the double-stranded anti-parallel duplex. A positive score is given for complementary base pairings, and a negative score is given for mispairings, openings and extensions of the transcription/replication gap (gap opening and gap extension). The scores, which were derived from the 5' end of the miRNA, were multiplied by a factor to express the importance of a perfect Watson-Crick base pairing which was observed experimentally. A Karlin-Altschul normalization was then carried out (miRBase Targets Version 3.0; online at microrna.sanger.ac.uk/targets/v3/).

MicroRNA Analyses in Failing Human Hearts

Using the methods already described above, miRNA expression profiles were established for n=4 diseased human hearts and n=4 healthy hearts. The diseased hearts comprise left-ventricular tissue which has been removed in the context of a heart transplant due to decompensated heart failure. The deregulated miRNAs (downregulation and upregulation), which represent potential target structures for new optimized treatments, are given below:

The following miRNAs are induced in decompensed human hearts (heart failure) (n=4 healthy left-ventricular tissue; n=4 diseased decompensated left-ventricular tissue):

hsa_miR_212 (SEQ ID No: 10), hsa_miR_21 (SEQ ID No: 14), hsa_miR_29b (SEQ ID No: 15), hsa_miR_129 (SEQ ID No: 16), mmu_miR_17_3p, hsa_miR_210, hsa_miR_29a, hsa_miR_299_5p, hsa_miR_211, hsa_miR_423, hsa_miR_320, hsa_miR_200c, hsa_miR_1, hsa_miR_15a, hsa_miR_213 (SEQ ID No: 17), hsa_miR_126_AS, hsa_let_7c (SEQ ID No: 18), hsa_miR_26a, hsa_miR_106b (SEQ ID No: 19), hsa_miR_130a, hsa_miR_384, hsa_miR_424, hsa_let_7e, hsa_let_7g, mmu_miR_199b, hsa_miR_125a, hsa_miR_199b, hsa_miR_28, hsa_miR_365, hsa_let_7d, hsa_miR_98, hsa_miR_335, hsa_let_7f, hsa_let_7b, hsa_miR_204, hsa_miR_372, hsa_miR_26b, mmu_miR_140_AS, hsa_miR_130b, mmu_miR_192, hsa_miR_34b, mmu_miR_129_3p, hsa_miR_132, hsa_miR_203, hsa_miR_181a, hsa_miR_127, mmu_miR_330, hsa_miR_15b, hsa_miR_199a, hsa_miR_516_3p, hsa_miR_101, hsa_miR_205, hsa_miR_151, hsa_miR_331, hsa_miR_32, hsa_miR_184, hsa_miR_489, hsa_miR_504, hsa_miR_31, hsa_miR_146a, hsa_miR_373, hsa_let_7a, hsa_miR_143, hsa_miR_511, hsa_miR_10b, hsa_miR_185, hsa_miR_136, rno_miR_349, hsa_miR_194, hsa_miR_145, hsa_miR_154, mmu_miR_151, hsa_miR_134 (SEQ ID No: 5), mmu_miR_424, hsa_miR_181c, mmu_miR_201, hsa_miR_508, hsa_miR_99b, hsa_miR_27b.

The following miRNAs are repressed in decompensated human hearts (heart failure) (n=4 healthy left-ventricular tissue; n=4 diseased decompensated left-ventricular tissue):

hsa_miR_139, hsa_miR_376a, hsa_miR_517a, hsa_miR_141, mmu_miR_380_3p, hsa_miR_30c, hsa_miR_520d, hsa_miR_519d, mmu_miR_291_3p, hsa_miR_221, hsa_miR_520b, hsa_miR_522, hsa_miR_422b, hsa_miR_527, hsa_miR_17_3p, hsa_miR_507, hsa_miR_24, hsa_miR_523, hsa_miR_452_AS, hsa_miR_520a_AS, hsa_miR_135b, hsa_miR_182, hsa_miR_215, hsa_miR_518f_AS, hsa_miR_224, hsa_miR_339, mmu_miR_292_5p, mmu_miR_376b, hsa_miR_222, hsa_miR_96, mmu_miR_290 (SEQ ID No: 24), hsa_miR_30a_5p (SEQ ID No: 25), hsa_miR_425, hsa_miR_219 (SEQ ID No: 26), hsa_miR_302b, hsa_miR_515_5p (SEQ ID No: 27), hsa_miR_526b (SEQ ID No: 28), hsa_miR_302b_AS, hsa_miR_107, hsa_miR_124a, hsa_miR_30b (SEQ ID No: 29).

An Overexpression of Certain miRNAs Leads to Cellular Hypertrophy and Activation of Fetal Pathological Gene Programs in Cardiomyocytes Cardiomyocytes were isolated from neonatal rats and cultured as described (Burkard et al., 2005). More than 95% of the cultured cells exhibited an expression for the cardiomyocyte-specific actinin, making it possible to conclude a very high purity of the cell culture. Fluorescent dye (Cy3)-labeled scrambled-miR, -miR-21, -miR-129 and -miR-212 molecules (Cy3-pre-miR miRNAs, Ambion, USA, 100 nM, 48 h) were transfected separately or in combination using a liposomal transfection method (Lipofectamine, Invitrogen, Germany) into cultured cardiomyocytes (Thum et al., 2007; FIGS. 5A, B). 48 h after transfection, cell lysates were produced from the cells as described (Thum et al., 2006). Adult cardiomyocytes were isolated and cultured as described (Thum et al., 2001). Adult cardiomyocytes were identified on the basis of their typical rectangular morphology, and the purity of the cell culture in terms of adult cardiomyocytes was very high (FIG. 6A). Adult cardiomyocytes were transfected liposomally with scrambled Cy3-labeled miRNA or a set of miRNAs (miR-21, miR-129 and miR-212, 72 h, 25 nM) (Lipofectamine, Invitrogen, Germany). As a marker for the cell size, the surface of the cultured neonatal (48 h after transfection) and adult (72 h after transfection) cardiomyocytes was determined using the image analysis program Axio-Vison Rel. 4.4 (Carl Zeiss GmbH, Germany). Statistical analyses were carried out by means of one-way ANOVA followed by a number of comparisons using the "Fisher's protected least-significant difference" test. The statistical analysis was carried out using the program StatView 5.0 (Abacus Concepts, Berkley, Calif., USA). The statistical significance was assumed as $P<0.05$.

Figure 5:
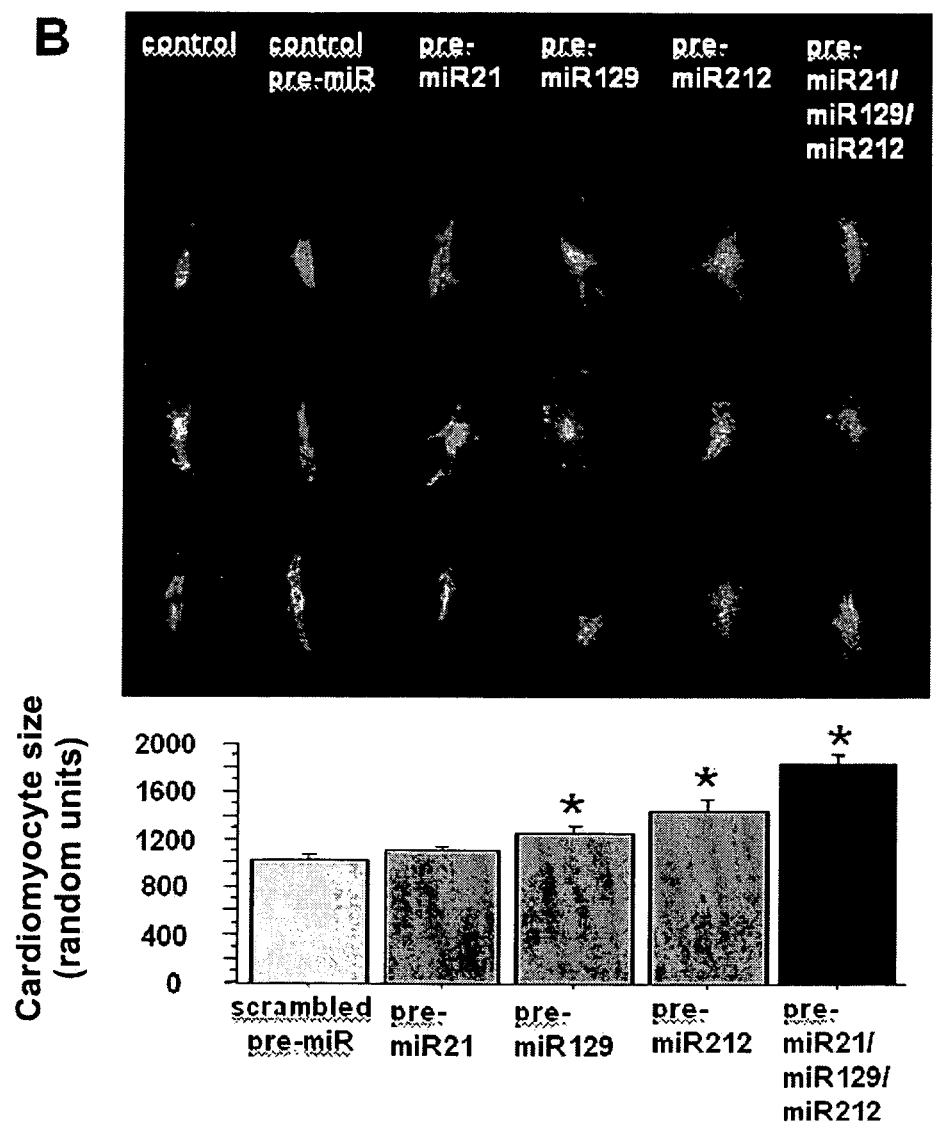
FIG. 5 shows miRNAs in cultured neonatal cardiomyocytes (to >90%; remaining cells are cardiac fibroblasts and endothelial cells) (A). The cell nuclei were stained with 4',6-diamidino-2-phenylindole (DAPI). B) Increase in cell size under miRNA treatment. C) Increased expression of individual miRNAs after miRNA transfection. D) Activation of fetal gene programs after miRNA transfection (ANP=atrial natriuretic peptide, BNP=brain natriuretic peptide; beta-MHC=beta-myosin heavy chain; cspg2=chondroitin sulfate proteoglycan 2; phlda1=pleckstrin homology-like domain, family A, member 1; HSP90=heat shock protein 90; RASA1=RAS p21 protein activator 1; MEF2a=myosin enhancer factor 2 alpha; cradd=CASP2 and RIPK1 domain containing adaptor with death domain; dtna=dystrobrevin alpha).
Figure 5:
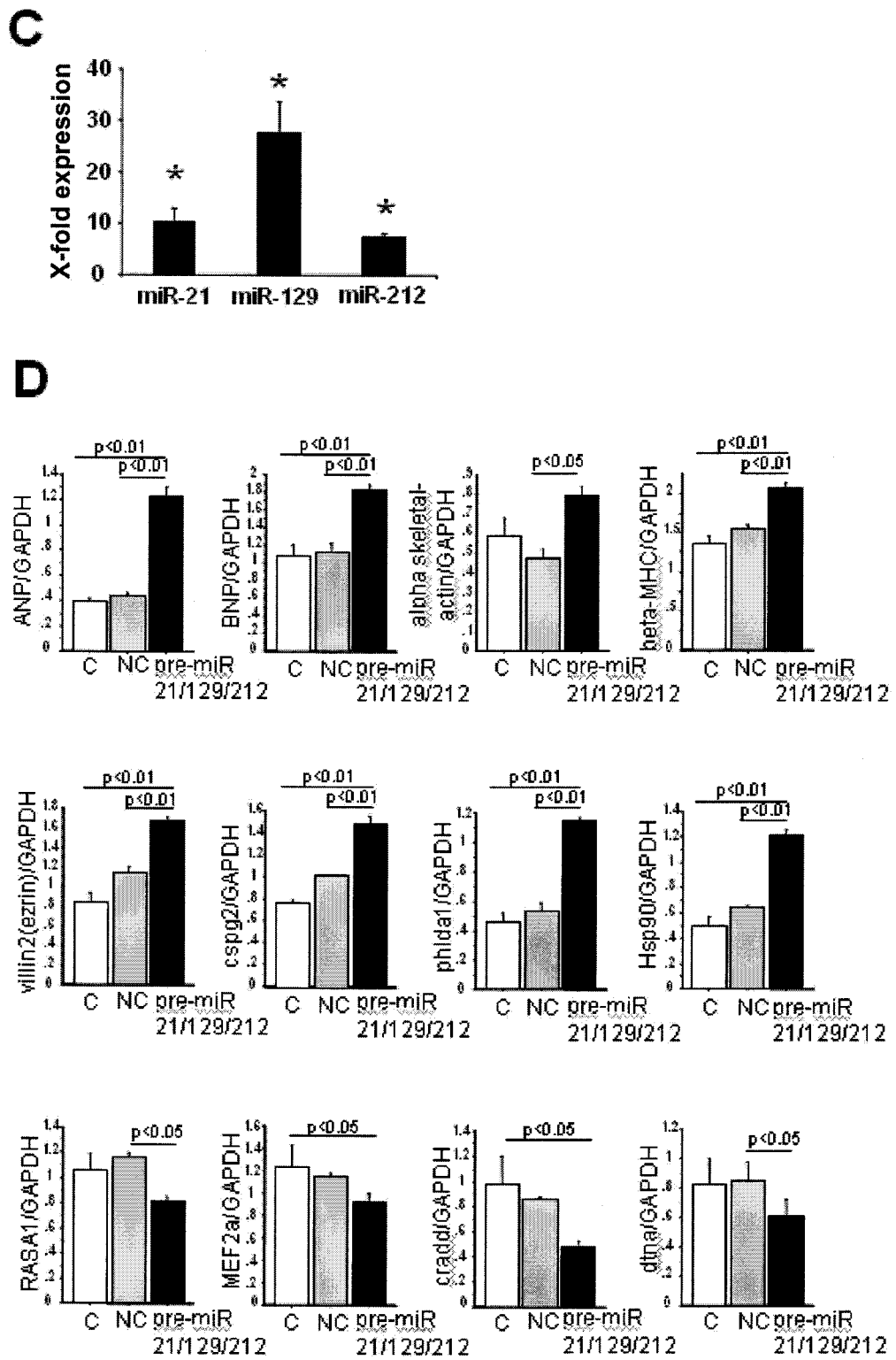
Figure 6:
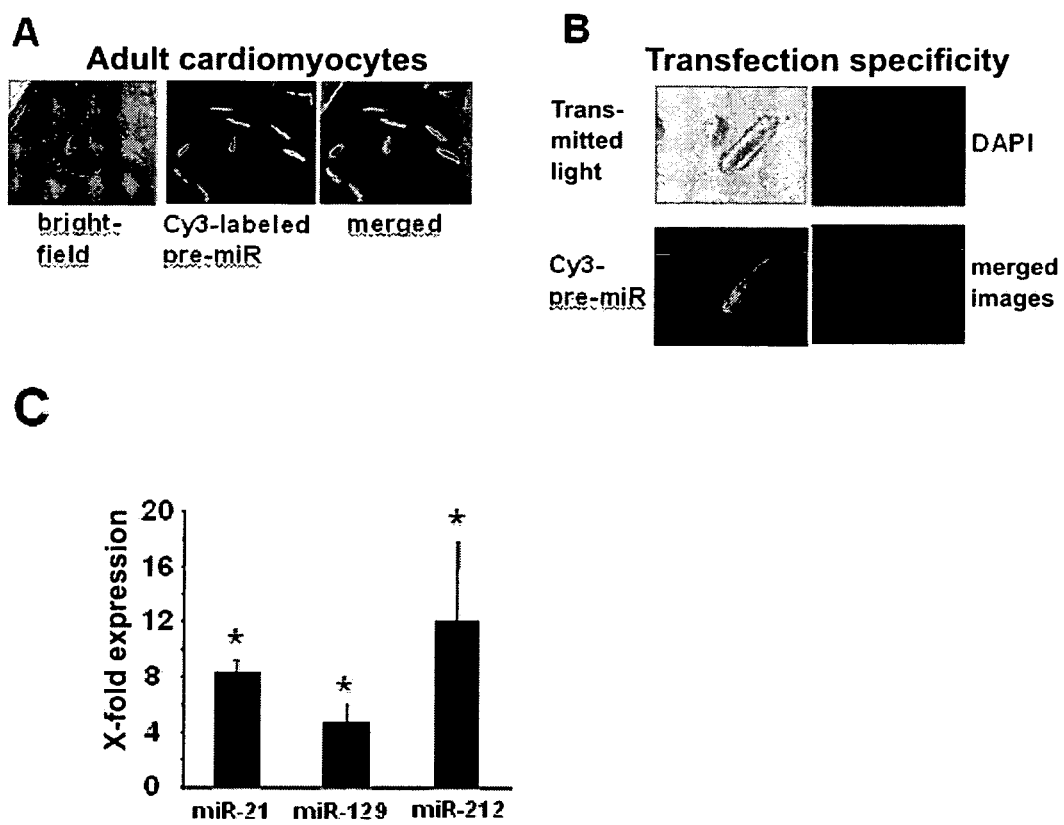
FIG. 6 shows miRNAs in cultured adult cardiomyocytes (to >90%; remaining cells are cardiac fibroblasts and endothelial cells) (A), the transfection specificity (B), the increased expression of individual miRNAs after miRNA transfection (C), an increase in cell size under miRNA treatment (D and F), and the activation of fetal gene programs after miRNA transfection (E). The cell nuclei were stained with 4',6-diamidino-2-phenylindole (DAPI). (The abbreviations are as specified above.)
Figure 6:
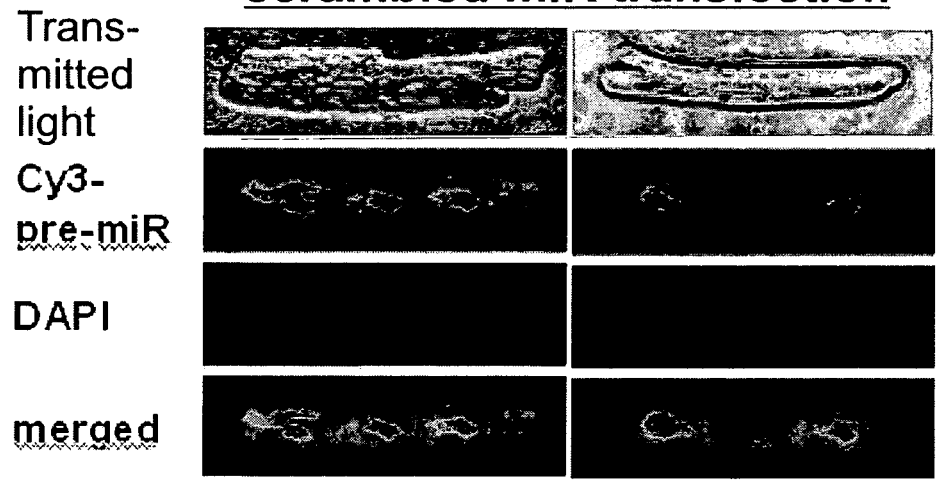
Figure 6:
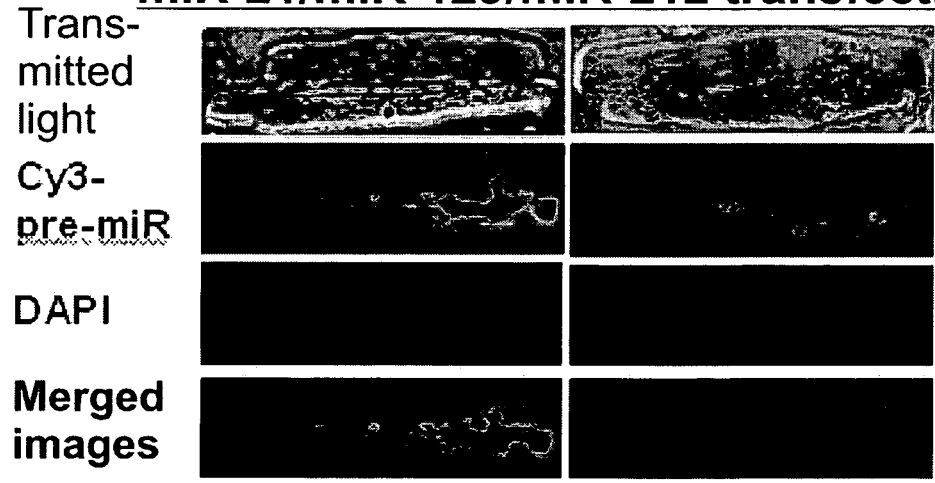
Figure 6:
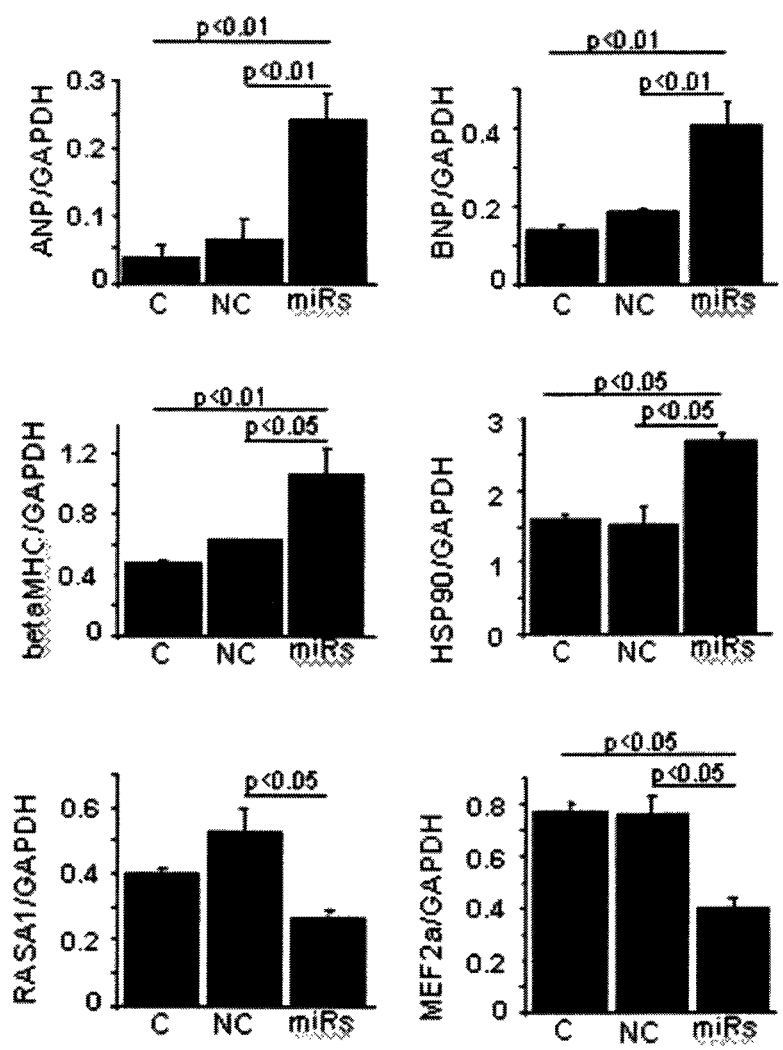

In order to analyze the importance of individual deregulated miRNAs for the biology of cardiomyocytes, three miRNAs (miR-21, miR-129 and miR-212) which are upregulated in failing human hearts were overexpressed in neonatal and adult cardiomyocytes (see FIGS. 5, 6). The transfection efficiency was analyzed by using Cy-3-labeled pre-miRNA molecules and was very high both in neonatal and in adult cardiomyocytes (see FIGS. 5A, B; FIG. 6A; >85%). In addition, after transfection, the expression of the individual miRNAs was determined by means of quantitative miRNA stem loops RT-PCR (TaqMan® MicroRNA Assays, Applied Biosystems, USA). In neonatal and adult cardiomyocytes, transfection led to an upregulation of the miRNAs miR-21, miR-129 and miR-212 (FIGS. 5C, 6C). Only vital cardiomyocytes were able to be transfected (FIG. 6B). While the overexpression of individual miRNAs had considerable effects on the cellular morphology, including hypertrophy, the greatest effect was able to be achieved by the simultaneous overexpression of all three miRNAs (miR-21, miR-129 and miR-212) (FIGS. 5B, 6D). Another consequence of the overexpression of these miRNAs was a reactivation of fetal gene programs, which usually occurs during a heart disease, including cardiac hypertrophy and heart failure. For instance, expression of the genes ANP, BNP, beta-MHC, alpha skeletal actin, villin2, cspg2, phlda1, hsp90, RASA1, MEF2a, cradd and dtna was modulated by the miRNA overexpression in such a way that the expression level was that of the diseased heart (FIGS. 5D, 6E). Transfection of adult cardiomyocytes with this set of miRNAs (miR-21, miR-129 and miR-212) likewise resulted in the onset of cellular hypertrophy and activation of fetal gene programs (FIGS. 6D, E, F). Transfection of scrambled miRNAs neither led to cellular hypertrophy nor to activation of fetal, pathological gene programs (FIGS. 5, 6).

The data identify certain miRNAs as important regulators for the reactivation of fetal gene programs in failing human hearts and thus make an important contribution with regard to explaining the transcriptional changes in the case of heart failure.

Figure 4:
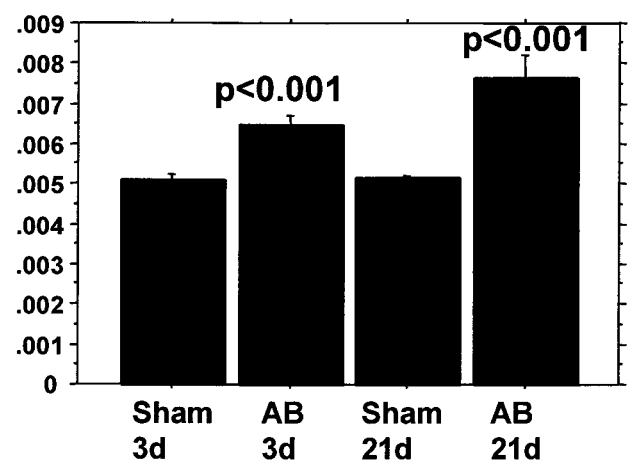
FIG. 4 shows the increase in left-ventricular weight after the constriction of the aorta (aortic banding) after 3 days (AB 3d) and 21 days (AB 21d) compared to the sham controls (Sham).

MicroRNA Analyses During the Development of Myocardial Hypertrophy on the Mouse Model In Vivo and In Vitro In-vivo: By means of an operative intervention, the diameter of the aorta on mice was greatly reduced ("aortic banding"). In the controls ("sham"-operated animals), the thorax was likewise opened and the aorta was displayed, but no constriction of the aorta was carried out. After 3 and 21 days, the left-ventricular heart weight relative to the total weight of the respective mouse was determined (see FIG. 4) and then the miRNA was isolated as described above. Thereafter, the miRNA expression profiles of the animals with a constricted aorta ("aortic banding animals") compared to the "sham"-operated animals after 3 and 21 days were established. The deregulated miRNAs (upregulation and downregulation) represent potential target structures for new optimized treatments.

The following miRNAs are induced after 3 days of "aortic banding" (n=4 animals per group):

mmu_miR_106a, hsa_miR_21, hsa_miR_223, hsa_miR_512_3p, hsa_miR_377, mmu_miR_376b, hsa_miR_379, hsa_miR_197, hsa_miR_522, ambi_miR_7026, mmu_miR_295, hsa_miR_326, hsa_miR_214, ambi_miR_7027, mmu_miR_329, hsa_miR_488, mmu_miR_215, hsa_miR_521, rno_miR_20_AS, hsa_miR_491, hsa_miR_200a, hsa_miR_520a_AS, mmu_miR_376a, hsa_miR_301, hsa_miR_221, hsa_miR_510, hsa_miR_371, rno_miR_336, hsa_miR_520d, hsa_miR_20a, hsa_miR_380_3p, hsa_miR_323, mmu_miR_201, hsa_miR_365, hsa_miR_518a, mmu_miR_101b, hsa_miR_17_5p, hsa_miR_196b, hsa_miR_224, hsa_miR_217, hsa_miR_507, hsa_miR_520d_AS, hsa_miR_196a, hsa_miR_367, hsa_miR_369_3p, hsa_miR_99a, hsa_miR_141, ambi_miR_7039, hsa_miR_212, hsa_miR_524, hsa_miR_345, hsa_miR_220, mmu_miR_202, hsa_miR_106a, hsa_miR_107, hsa_miR_99b, hsa_miR_30b, hsa_miR_23b, hsa_miR_342, hsa_miR_518f, hsa_miR_339, hsa_miR_338, hsa_miR_302a.

The following miRNAs are repressed after 3 days of "aortic banding" (n=4 animals per group):

hsa_let_7d, hsa_miR_30a_5p, hsa_miR_130a, ambi_miR_7089, hsa_miR_106b, hsa_miR_503, hsa_miR_485_5p, hsa_miR_496, hsa_miR_25, hsa_miR_493, ambi_miR_7081, hsa_miR_520h, hsa_miR_105, hsa_miR_490, hsa_miR_505, hsa_miR_452_AS, ambi_miR_7085, hsa_miR_101, ambi_miR_7083, hsa_miR_216, ambi_miR_7080, hsa_miR_500, rno_miR_346, ambi_miR_7066, ambi_miR_7105, ambi_miR_7067, hsa_miR_497, hsa_miR_429, hsa_miR_302b_AS, hsa_miR_182, ambi_miR_7058, hsa_miR_499, hsa_miR_452, hsa_miR_511, hsa_miR_519b, hsa_miR_494, mmu_miR_140_AS, ambi_miR_7068_1, ambi_miR_7097, hsa_miR_337, hsa_miR_133a, ambi_miR_7059_1, hsa_miR_502, hsa_miR_202_AS, hsa_miR_432_AS, rno_miR_352, hsa_let_7b, mmu_miR_290, ambi_miR_7084, rno_miR_349, hsa_let_7f, hsa_miR_504, hsa_miR_126, hsa_miR_1, mmu_miR_7b, mmu_miR_34b, hsa_miR_150, hsa_miR_30e_3p, hsa_miR_370, ambi_miR_7095, hsa_miR_190, hsa_miR_518c_AS, ambi_miR_7062, hsa_miR_375, mmu_miR_345, rno_miR_333, hsa_let_7a, hsa_miR_373, hsa_miR_495, hsa_miR_432, hsa_miR_492, mmu_miR_297, hsa_miR_515_3p, ambi_miR_7079, ambi_miR_7036, hsa_miR_372, mmu_miR_346, mmu_miR_17_3p, mmu_miR_350, mmu_miR_129_3p, mmu_miR_330, ambi_miR_7101, hsa_miR_145, ambi_miR_7070, mmu_miR_341, hsa_miR_325, ambi_miR_7076, hsa_miR_423, hsa_miR_135b, hsa_miR_422a, hsa_miR_34a, hsa_miR_34c, hsa_miR_142_5p, hsa_miR_30c.

The following miRNAs are induced after 21 days of "aortic banding" (n=4 animals per group):

hsa_miR_30a_5p, hsa_miR_106b, hsa_miR_25, hsa_miR_216, mmu_miR_297, hsa_miR_105, hsa_miR_101, hsa_miR_429, hsa_miR_512_3p, hsa_miR_138, hsa_miR_519b, mmu_let_7d_AS, hsa_miR_432, mmu_miR_341, hsa_miR_214, ambi_miR_7026, hsa_miR_222, hsa_miR_491, rno_miR_346, mmu_miR_291_3p, hsa_miR_524, rno_miR_327, ambi_miR_7039, mmu_miR_346, hsa_miR_367, mmu_miR_207, mmu_miR_351, mmu_miR_292_3p, hsa_miR_510, ambi_miR_7027, hsa_miR_379, hsa_miR_134, hsa_miR_525, hsa_miR_498, hsa_miR_198, hsa_miR_373, hsa_miR_512_5p, hsa_miR_136, hsa_miR_372, hsa_miR_518f, hsa_miR_514, hsa_miR_525_AS, hsa_miR_7, hsa_miR_506, hsa_miR_517a, ambi_miR_7085, mmu_miR_380_3p, hsa_miR_521, hsa_miR_130a, ambi_miR_7076, hsa_miR_296, hsa_miR_520d_AS, hsa_miR_346, hsa_miR_378, hsa_miR_324_3p, ambi_miR_7067, hsa_miR_520h, hsa_miR_206, hsa_miR_122a, hsa_miR_373_AS, mmu_miR_215, mmu_miR_409, hsa_miR_221, hsa_miR_330, ambi_miR_7089, hsa_miR_129, mmu_miR_294, hsa_miR_196a, mmu_miR_376b, mmu_miR_383, ambi_miR_7074, hsa_miR_187, mmu_miR_300, hsa_miR_302d, hsa_miR_375, mmu_miR_292_5p, hsa_miR_518a, hsa_miR_92, ambi_miR_7066, hsa_miR_424, hsa_miR_518f_AS, hsa_miR_302c, hsa_miR_193a, hsa_miR_507, mmu_miR_429, rno_miR_20_AS, hsa_miR_200b, hsa_miR_339, hsa_miR_369_3p, mmu_miR_217, hsa_miR_517_AS, hsa_miR_527, hsa_miR_326, hsa_miR_377, mmu_miR_411, rno_miR_333, mmu_miR_344, mmu_miR_295, rno_miR_7_AS, ambi_miR_7100.

The following miRNAs are repressed after 21 days of "aortic banding" (n=4 animals per group):

hsa_miR_183, rno_miR_352, hsa_miR_133a, hsa_miR_10a, hsa_miR_203, hsa_miR_1, hsa_miR_202_AS, hsa_miR_450, hsa_miR_126, hsa_let_7a, hsa_miR_100, hsa_let_7b, hsa_miR_26b, hsa_let_7f, hsa_miR_26a, mmu_miR_337, hsa_miR_30c, hsa_miR_23b, hsa_miR_499, hsa_miR_29a, hsa_miR_23a, hsa_miR_10b, hsa_miR_24, hsa_let_7g, hsa_miR_30d, hsa_miR_30e_5p, mmu_miR_129_3p, hsa_miR_29c, hsa_miR_16, hsa_miR_145, hsa_miR_15b, hsa_miR_142_5p, hsa_miR_422b, hsa_miR_524_AS, hsa_miR_189, mmu_miR_106a, hsa_miR_27a, hsa_miR_422a, rno_miR_336, hsa_miR_150, hsa_miR_9_AS, ambi_miR_7029, hsa_miR_380_3p, hsa_miR_153, hsa_miR_490, hsa_miR_135b, hsa_miR_212, hsa_miR_125b, hsa_miR_22, hsa_miR_374, hsa_miR_195, rno_miR_421, hsa_miR_200c, mmu_miR_151, ambi_miR_7059_1, hsa_let_7i, hsa_miR_140, hsa_miR_34a, hsa_miR_182, hsa_miR_501, hsa_miR_191, hsa_miR_342, hsa_miR_103, hsa_miR_27b, mmu_miR_140_AS, hsa_miR_204, hsa_miR_513, rno_miR_151_AS, hsa_miR_194, hsa_miR_125a, hsa_miR_345, hsa_miR_143, hsa_miR_15a, hsa_miR_520a, hsa_miR_36, hsa_miR_21, hsa_miR_219, hsa_miR_519e_AS, hsa_miR_497, hsa_miR_199a, hsa_miR_28, ambi_miR_7103, ambi_miR_7105, mmu_miR_298, hsa_miR_197, hsa_miR_503, hsa_miR_34c, hsa_miR_526b, hsa_miR_485_5p, hsa_miR_508, hsa_miR_489, hsa_miR_526b_AS, hsa_miR_493, mmu_miR_199b, hsa_miR_188, hsa_miR_518d, mmu_miR_345, hsa_miR_181c, hsa_miR_99b, mmu_miR_322, hsa_miR_523, mmu_miR_291_5p, hsa_miR_148b, hsa_miR_526c, hsa_miR_302b_AS, hsa_miR_520b, hsa_miR_29b, hsa_miR_152, hsa_miR_149, hsa_miR_18a, hsa_miR_106a, hsa_miR_205, ambi_miR_7055, hsa_miR_186, hsa_miR_432_AS, hsa_miR_185, ambi_miR_7062, ambi_miR_7080, hsa_let_7e, hsa_miR_192, mmu_miR_155, ambi_miR_7075, hsa_miR_30e_3p, hsa_miR_505, ambi_miR_7084, hsa_miR_494, ambi_miR_7083, ambi_miR_7068_1, hsa_miR_17_3p, ambi_miR_7036, hsa_miR_518c, hsa_miR_34b, hsa_miR_148a, mmu_miR_330, mmu_miR_7b, hsa_miR_496, ambi_miR_7101, hsa_miR_199a_AS, hsa_miR_492, hsa_miR_324_5p, ambi_miR_7038_1, ambi_miR_7081, hsa_miR_412, hsa_miR_182_AS, hsa_miR_211, hsa_miR_151, hsa_miR_452, hsa_miR_337, hsa_miR_502, hsa_miR_193b, hsa_miR_376a, hsa_miR_299_5p, ambi_miR_7097, hsa_miR_519e, hsa_miR_19a, hsa_miR_488, hsa_miR_449, hsa_miR_320, hsa_miR_208, hsa_miR_518e, hsa_miR_410, hsa_miR_124a, hsa_miR_135a, hsa_miR_184, hsa_miR_181a, hsa_miR_516_3p, hsa_miR_328.

In-Vitro Induction of Hypertrophy on Neonatal Cardiomyocytes

Firstly, neonatal cardiomyocytes from mice were isolated and cultured. A 48 h treatment with 10 µM each of phenylephrine and isoproterenol was then carried out, which led to a cellular hypertrophy of cultured cardiomyocytes (Buitrago et al., 2005). Thereafter, in this case too, miRNA expression profiles of treated and untreated (non-hypertrophied) cardiomyocytes were established. The deregulated miRNAs (up-regulation and downregulation) represent potential target structures for new optimized treatments of cardiac hypertrophy.

The following miRNAs are induced after 2 days' treatment (10 µM each of phenylephrine and isoproterenol) of cultured neonatal cardiomyocytes (n=3 tests per group):

hsa_miR_302c_AS, hsa_miR_101, hsa_miR_124a, hsa_miR_33, hsa_miR_220, hsa_miR_154, hsa_miR_99a, hsa_miR_340, hsa_miR_216, hsa_miR_323, hsa_miR_107, hsa_miR_302a, hsa_miR_141, hsa_miR_224, hsa_miR_98, hsa_miR_217, hsa_let_7c, hsa_miR_203, hsa_miR_213, mmu_miR_424, mmu_miR_106a, hsa_miR_302c, mmu_miR_217, hsa_miR_302b, hsa_miR_144, hsa_miR_32, hsa_miR_339, hsa_miR_205, hsa_miR_488, mmu_miR_291_3p, hsa_miR_17_3p, hsa_miR_338, hsa_miR_518a, hsa_miR_142_5p, mmu_miR_292_5p, hsa_miR_219, hsa_miR_302d, ambi_miR_7027, hsa_miR_384, hsa_miR_139, hsa_miR_137, hsa_miR_96, mmu_miR_292_3p, hsa_miR_136, hsa_miR_208, mmu_miR_17_3p, hsa_miR_18a, hsa_miR_215, hsa_miR_9, hsa_miR_142_3p, hsa_miR_181c, mmu_miR_140_AS, hsa_miR_130b.

The following miRNAs are repressed after 2 days' treatment (10 µM each of phenylephrine and isoproterenol) of cultured neonatal cardiomyocytes (n=3 tests per group):

hsa_let_7d, hsa_miR_193b, ambi_miR_7080, hsa_miR_490, hsa_miR_497, ambi_miR_7081, hsa_miR_493, ambi_miR_7075, hsa_miR_502, hsa_miR_526c, hsa_miR_491, hsa_miR_199a_AS, ambi_miR_7097, hsa_miR_485_5p, hsa_miR_501, hsa_miR_195, hsa_miR_505, hsa_miR_199a, mmu_miR_337, hsa_miR_30e_5p, hsa_miR_191, hsa_miR_489, hsa_miR_520e, mmu_miR_345, hsa_miR_189, hsa_miR_526b, hsa_miR_452, hsa_miR_432_AS, hsa_miR_30a_5p, hsa_miR_374, hsa_miR_496, ambi_miR_7068_1, hsa_miR_370, hsa_miR_34b, hsa_miR_499, mmu_miR_298, ambi_miR_7076, mmu_miR_7b, hsa_miR_30b, hsa_miR_524_AS, hsa_miR_188, ambi_miR_7062, hsa_miR_130a, hsa_miR_382, rno_miR_346, hsa_miR_515_5p, hsa_miR_520a, hsa_miR_519c, hsa_miR_513, hsa_miR_526b_AS, hsa_miR_512_5p, ambi_miR_7059_1, hsa_miR_204, ambi_miR_7084, ambi_miR_7105, hsa_miR_23b, hsa_miR_500, hsa_miR_34c, hsa_miR_518c, hsa_miR_410, hsa_miR_492, ambi_miR_7095, hsa_miR_202_AS, hsa_miR_380_5p, ambi_miR_7054, hsa_miR_25, hsa_miR_518b, hsa_miR_432, hsa_miR_30d, hsa_miR_449, hsa_miR_181a, hsa_miR_450, ambi_miR_7055, hsa_miR_29a, hsa_miR_19a, rno_miR_347, hsa_miR_373_AS, ambi_miR_7083, hsa_miR_34a, hsa_miR_7, hsa_miR_24, rno_miR_421, mmu_miR_383, rno_miR_336, hsa_miR_181b, ambi_miR_7103, rno_miR_349, hsa_miR_361, mmu_miR_429, mmu_miR_384, hsa_miR_100, hsa_miR_519e_AS, mmu_miR_409, hsa_miR_199b, ambi_miR_7101, hsa_miR_15b, hsa_miR_371, hsa_miR_151, hsa_miR_19b, mmu_miR_351, hsa_miR_99b, hsa_miR_508, hsa_miR_140, mmu_miR_346.

The different methods employed and pathophysiological conditions (human heart failure, rat infarct model, mouse hypertrophy model caused by "aortic banding" after 3 and 21 days, pharmacological in-vitro model of cardiac hypertrophy) lead to results in terms of miRNA expression which follow the same trends.

The most effective miRNA candidates were selected according to the following criteria:

(1) The choice of induced miRNAs after chronic myocardial infarction took place on the basis of the level of induction after myocardial infarction (more than approx. 2-fold induced), and also on the basis of the expected regulated target genes of the respective miRNA (e.g. miRNA-212).

(2) The choice of induced miRNAs in cardiac hypertrophy and heart failure took place according to the following criteria:
  (a) more than approx. 1.2-fold induction in the human hearts of patients with heart failure, and
  (b) at least one further induction in one of the additionally employed models (aortic banding after 3d and 21d; pharmacological in vitro hypertrophy model).

The SEQ ID Nos, the name from the database (Sanger) and the MI references are summarized in the following Table 2.

TABLE 2

| SEQ ID No. | Name (Sanger) | MI reference |
| --- | --- | --- |
| SEQ ID No: 1 | miR-15b | MI 0000438 |
| SEQ ID No: 2 | miR-23a | MI 0000079 |
| SEQ ID No: 3 | miR-126* | MI 0000471 |
| SEQ ID No: 4 | miR-128a | MI 0000155 |
| SEQ ID No: 5 | miR-134 | MI 0000474 |
| SEQ ID No: 6 | miR-149 | MI 0000478 |
| SEQ ID No: 7 | miR-151 | MI 0000809 |
| SEQ ID No: 8 | miR-206 | MI 0000490 |
| SEQ ID No: 9 | miR-211 | MI 0000287 |
| SEQ ID No: 10 | miR-212 | MI 0000288 |

TABLE 2-continued

| SEQ ID No. | Name (Sanger) | MI reference |
| --- | --- | --- |
| SEQ ID No: 11 | miR-214 | MI 0000290 |
| SEQ ID No: 12 | miR-328 | MI 0000804 |
| SEQ ID No: 13 | miR-371 | MI 0000779 |
| SEQ ID No: 14 | miR-21 (hsr miR-21) | MI 0000077 |
| SEQ ID No: 15 | miR-29b-1 | MI 00000105 |
| SEQ ID No: 16 | miR-129 | MI 0000252 |
| SEQ ID No: 17 | miR-213 | MI 0000289 |
| SEQ ID No: 18 | let-7c | MI 0000064 |
| SEQ ID No: 19 | miR-106b | MI 0000734 |
| SEQ ID No: 20 | miR-182 | MI 0000272 |
| SEQ ID No: 21 | miR-296 | MI 0000747 |
| SEQ ID No: 22 | miR-122a | MI 0000442 |
| SEQ ID No: 23 | miR-30a-3p | MI 0000088 |
| SEQ ID No: 24 | miR-290 | MI 0000388 |
| SEQ ID No: 25 | miR-30a__5p | MI 0000088 |
| SEQ ID No: 26 | miR-219 | MI 0000296 |
| SEQ ID No: 27 | miR-515__5p | MI 0003144 |
| SEQ ID No: 28 | miR-526b | MI 0003150 |
| SEQ ID No: 29 | miR-30b | MI 0000441 |

The most preferred miRNAs are summarized again below:
Upregulated miRNAs
(1) miR-212 (SEQ ID No: 10)
This miRNA is upregulated in particular in human heart failure (5.6-fold) and after chronic myocardial infarction (2.4-fold) in rats.
(2) miR-214 (SEQ ID No: 11)
This miRNA is upregulated slightly in human heart failure (1.2-fold) and clearly early and late after cardiac hypertrophy (aortic banding 3 and 21 days) (1.5-fold and 2.1-fold, respectively) in mice and also after chronic myocardial infarction (2.6-fold) and after pharmacological cardiac hypertrophy induction in vitro (1.5-fold).
(3) miR-21 (SEQ ID No: 14)
This miRNA is upregulated in particular in human heart failure (3.3-fold) and early after cardiac hypertrophy (aortic banding 3 days) (3.0-fold) in mice.
(4) miR-134 (SEQ ID No: 5)
This miRNA is upregulated slightly in human heart failure (1.2-fold) and clearly late after cardiac hypertrophy (aortic banding 21 days) (1.7-fold) in mice and also after chronic myocardial infarction (3.3-fold) in rats.
(5) miR-129 (SEQ ID No: 16)
This miRNA is upregulated in human heart failure (2.7-fold) and late after cardiac hypertrophy (aortic banding 21 days) (1.4-fold) in mice and also after chronic myocardial infarction (1.4-fold) in rats.
Downregulated miRNAs
(6) miR-182 (SEQ ID No: 20)
This miRNA is downregulated in human heart failure (−1.3-fold) and clearly early and late after cardiac hypertrophy (aortic banding 3 and 21 days) (−1.8-fold and −2.2-fold, respectively) in mice and also after chronic myocardial infarction (−4.0-fold) in rats.
(7) miR-290 (SEQ ID No: 24)
This miRNA is downregulated in human heart failure (−1.4-fold) and early after cardiac hypertrophy (aortic banding 3 days) (−1.6-fold) in mice and also after chronic myocardial infarction (−1.4-fold) in rats.

Mir-21 as a Particularly Suitable Therapeutic Target

Figure 7:
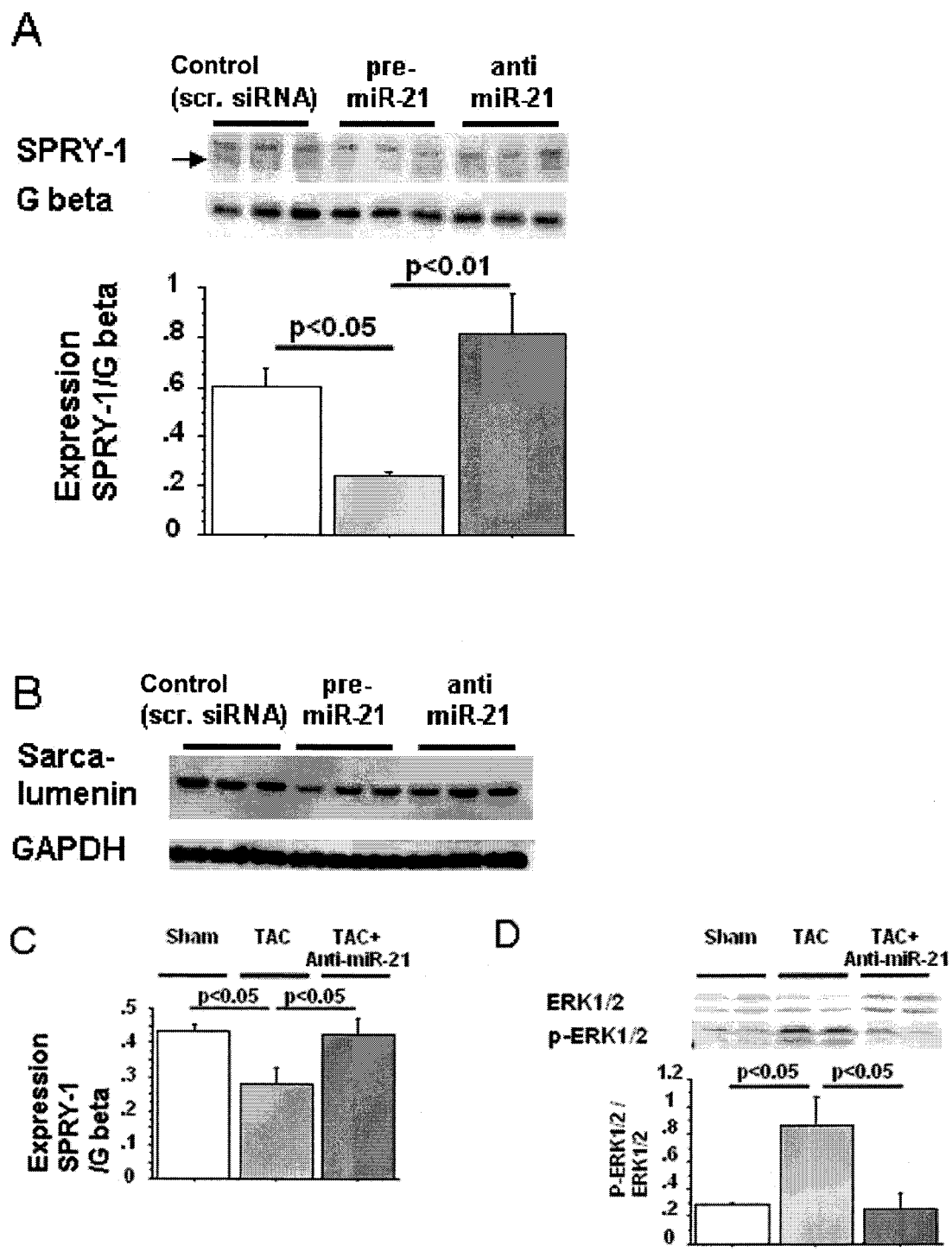
FIG. 7 shows the repression of Sprouty 1 (A) and sarcalumenin (B) after pre-mir-21 overexpression in cultured cardiomyocytes (to >90%; remaining cells are cardiac fibroblasts and endothelial cells). (C) and (D) show the repression of Sprouty 1 and the increased ERK1/2 phosphorylation after pressure loading of the left ventricle in the animal model (aortic banding). (E) shows the uptake of intravenously injected Cy-3-labeled Antagomir® in the heart. (F) shows a repression of cardiac miR-21 expression after Antagomir®-21 treatment. (G) shows an increase in the weight of the heart relative to the weight of the animal three weeks after aortic banding, and also the prevention of the increase in weight of the heart under Antagomir®-21 treatment. (AB or TAC=Aortic Banding Operation; anti-21 or Anti-miR-21=Antagomir®-21 treatment).
Figure 7:
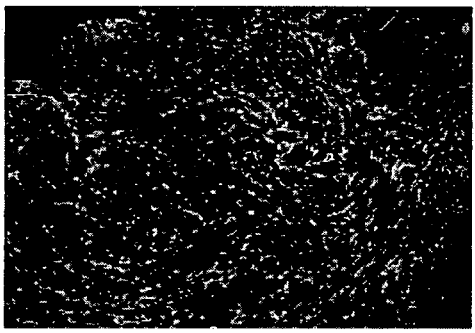
Figure 7:
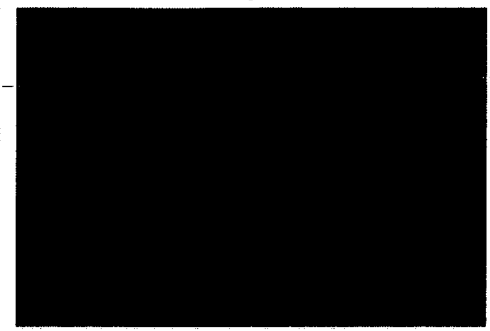
Figure 7:
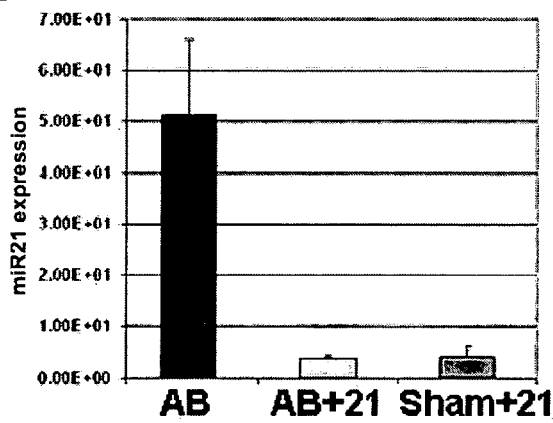
Figure 7:
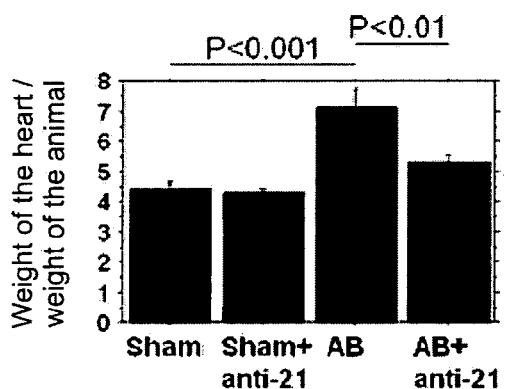

After inducing hypertrophy on the mouse model, the inventors discovered an increased expression of miR-21 (see above). They therefore examined whether an inhibition of miR-21 in vivo prevents the development of cardiac hypertrophy due to pressure loading (reducing the diameter of the aorta by means of an aortic banding operation). They firstly made use of bioinformatic analyses and used the miRBase database (online at microrna.sanger.ac.uk/) to search for potential targets with binding sites for miR-21 in their 3' non-translated regions. Here they identified Sprouty 1 (SPRY1; access number: NM_001097524), sarcalumenin (access number: NM_001098814) and tropomyosin (access number: then NM_001018005) as potential miR-21 targets. In particular the 3' non-translated region of SPRY1-mRNA contains a number of conserved miR binding sites, one of which is a binding site for miR-21 which is upregulated in the heart in cardiac hypertrophy and heart failure. In order to examine a direct role of miR-21 in the post-transcriptional regulation of SPRY1 and sarcalumenin, the inventors transfected pre-miR-21 molecules (Ambion, pre-miRs, 50 nM, 72 h) into cultured cardiomyocytes and analyzed the SPRY1 and sarcalumenin protein expression. They observed a significant reduction in the protein expression of SPRY1 and sarcalumenin after pre-miR21 overexpression in cultured cardiomyocytes (FIGS. 7A, B). A reduction in these proteins very probably leads to the development of cardiac hypertrophy and cardiac dysfunction after pressure loading of the left ventricle. The inventors also observed a reduced protein expression of SPRY1 (FIG. 7C) and an increased phosphorylation of the extracellular signal-regulated kinase 1/2 (phospho-ERK1/2) after pressure loading in the left ventricle of mice (FIG. 7D).

The inventors then injected, via a catheter inserted into the Vena jugularis, chemically modified oligonucleotides for a specific downregulation of the endogenous miR-21 expression (Antagomir®-21, Alnylam). The Antagomir® sequences were synthesized as reverse complementary oligonucleotides, as described in the literature, with Antagomir®-181a additionally being labeled with Cy3 dye (Krutzfeldt et al., 2005).

Figure 8:
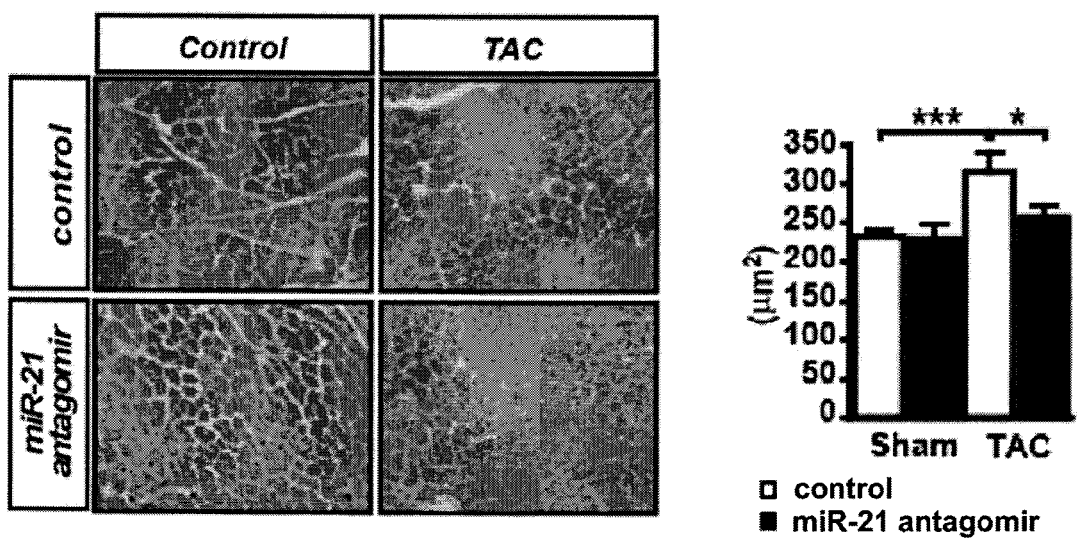
FIG. 8A shows an increase in size of the cardiomyocytes after aortic banding and the normalization under Antagomir®-21 treatment. (B) shows echocardiographic analyses after aortic banding with and without Antagomir®-21 treatment. (The abbreviations are as specified above.)
Figure 8:
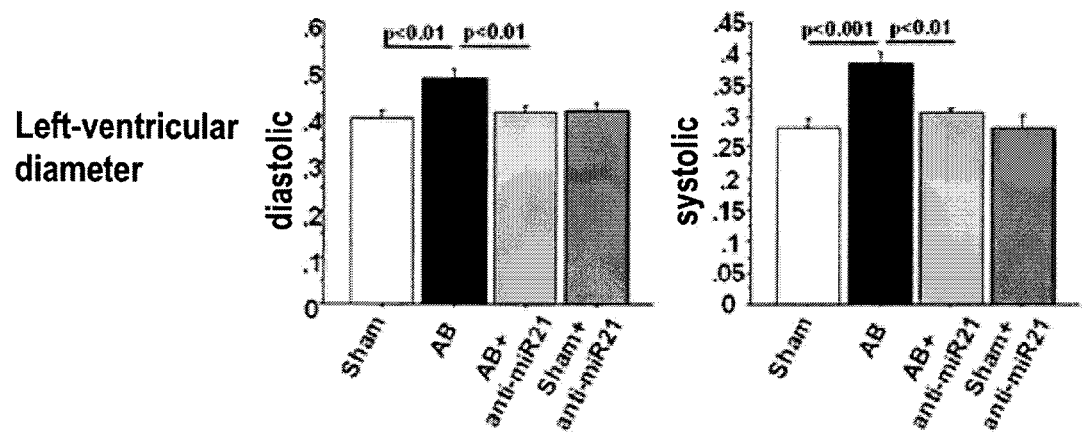
Figure 8:
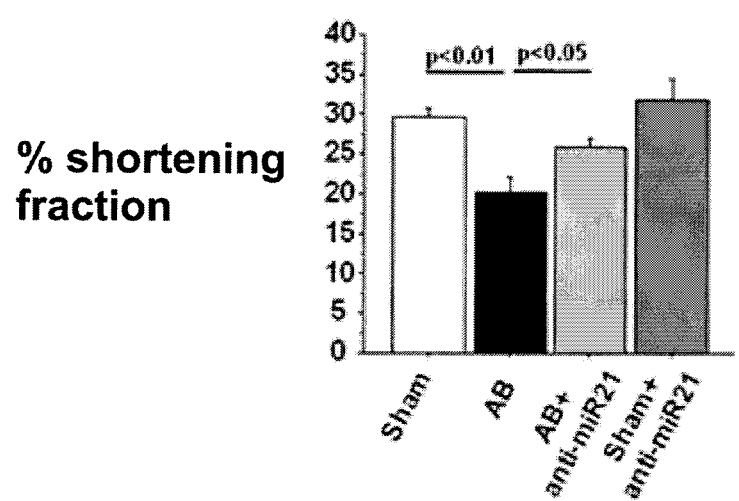

Treatment was started 24 h after the operative reduction of the aorta diameter (aortic banding). Each morning, 80 mg/kg/d were then applied intravenously for 3 days 1× per day. After injection of a Cy-3-labeled Antagomir®, 3 hours later the heart was removed and the cardiac uptake of the C3-labeled Antagomir® was analyzed by means of immunofluorescence. A significant uptake of the Antagomir® into the heart could be detected (FIG. 7E). Even after 3 weeks, real-time PCR analyses surprisingly showed significant repression of cardiac miR-21 expression after an initial 3-day Antagomir®-21 treatment (FIG. 7F). Besides the repression of cardiac miR-21 expression, this treatment led to an increase in SPRY1 protein expression after the aortic banding operation (FIG. 7C). The increase in expression of phospho-ERK1/2 which was observed after aortic banding was prevented completely as a result of the 3-day Antagomir®-21 treatment (FIG. 7D). The heart weight normalized to the body weight increased significantly 3 weeks after aortic banding and was nevertheless completely normalized as a result of the Antagomir®-21 treatment (FIG. 7G). The increase in the size of the myocytes in sections of the heart 3 weeks after the aortic banding operation was able to be completely inhibited by the Antagomir®-21 treatment (FIG. 8A). An Antagomir®-21 treatment in sham-operated mice did not lead to any change in the heart weight or in the size of the myocytes (FIGS. 7G, 8A). The cardiac function was analyzed by means of echocardiography and catheter-based volume/pressure measurements. Both the left-ventricular end-systolic and end-diastolic diameter increased 3 weeks after aortic banding, whereas fractional shortening (an indication of cardiac function) was considerably restricted (FIG. 8B). The pressure loading of the left ventricle brought about by aortic banding led to a measurable increase in the left-ventricular end-diastolic pressure (LVEDp; 2.8±1.3 mmHg (sham) versus 7.2±1.7 mmHg (aortic banding); p=0.09) and to a reduced cardiac ejection fraction (55.9%±8.0% (sham) versus 24.7%±5.6% (aortic banding); p<0.05). The Antagomir®-21 treatment after aortic banding surprisingly prevented the left-ventricular dilatation and normalized the fractional shortening (FIG. 8B). After the Antagomir®-21 treatment, the ejection fraction was also improved and the left-ventricular end-diastolic pressure was normalized (EF: 50.1%±13.1%; LVEDp: 2.4±1.5 mmHg).

Examples of Embodiments on Humans—Treatment

A modulation of miRNAs in the cardiovascular system could also be used successfully in humans to prevent or as a treatment for cardiovascular diseases, such as cardiac hypertrophy, heart failure or myocardial infarction. Substances which increase or prevent miRNA expression in the cardiovascular system can be applied via various routes, such as for example intravenously, intra-arterially, intracardially via catheters or during open heart surgery, subcutaneously, transdermally, by inhalation, orally, rectally, etc. The treatment could be carried out on patients with cardiac hypertrophy, after myocardial infarction or on patients with acute or chronic heart failure or coronary heart disease. In view of the previous experimental in vitro and animal studies carried out by the inventors, the prevention of the expression of miR-21, miR-129 and miR-212 appears to be promising as a causal therapeutic approach to prevent various cardiovascular diseases.

Examples of Embodiments on Humans—Diagnosis

The data demonstrate that a change in the cardiac expression of various miRNAs precedes the development of a heart disease, in particular cardiac hypertrophy and heart failure. In order to determine the expression of miRNAs in the heart of patients, a myocardial biopsy may be performed. From this, the miRNA can be isolated and the expression level can be determined. An increase in individual miRNAs or in the combination thereof, particularly miR-21 (SEQ ID No: 14), miR-129, miR-212 (SEQ ID No: 10), miR-214 (SEQ ID No: 11), miR-134 (SEQ ID No: 5), can be used to diagnose an increased risk of development or already the existence of cardiac hypertrophy and/or heart failure. A downregulation of miR-182 (SEQ ID No: 20) or miR-290 (SEQ ID No: 24) or of the combination thereof can be used to diagnose an increased risk of development or already the existence of cardiac hypertrophy and/or heart failure. Likewise, the combination of an increased expression of miR-21 (SEQ ID No: 14), miR-129, miR-212 (SEQ ID No: 10), miR-214 (SEQ ID No: 11), miR-134 (SEQ ID No: 5) with a reduced expression of miR-182 (SEQ ID No: 20) or miR-290 (SEQ ID No: 24) can be used to diagnose an increased risk of development or already the existence of cardiac hypertrophy and/or heart failure. The expression level of the respective miRNAs may be determined either via microarray analyses, RT-PCR, Northern blotting, or other suitable methods.

REFERENCES

Buitrago M, Lorenz K, Maass A H, Oberdorf-Maass S, Keller U, Schmitteckert E M, Ivashchenko Y, Lohse M J, Engelhardt S. The transcriptional repressor Nab1 is a specific regulator of pathological cardiac hypertrophy. Nat. Med. 2005 August; 11(8):837-44.

Burkard N, Becher J, Heindl C, Neyses L, Schuh K, Ritter O. (2005) Targeted proteolysis sustains calcineurin activation. Circulation 111:1045-53

Harfe, B. D. (2005). MicroRNAs in vertebrate development. Curr Opin Genet Dev 15, 410-415.

Hornstein, E., Mansfield, J. H., Yekta, S., Hu, J. K.-H., Harfe, B. D., McManus, M. T., Baskerville, S., Bartel, D. P., and Tabin, C. J. (2005). The microRNA miR-196 acts upstream of Hoxb8 and Shh in limb development. Nature 438, 671-674.

Huber W, von Heydebreck A, Sueltmann H, Poustka A, Vingron M: Variance stabilization applied to microarray data calibration and to the quantification of differential expression. Bioinformatics 2002, 18:96-104

Hunter J J, G. A., Chien K R (1999). Molecular and cellular biology of cardiac hypertrophy and failure (Philadelphia: W. B. Saunders).

Hutvagner, G., and Zamore, P. D. (2002). A microRNA in a multiple-turnover RNAi enzyme complex. Science 297, 2056-2060.

Krutzfeldt J, Rajewsky N, Braich R, Rajeev K G, Tuschl T, Manoharan M, Stoffel M. (2005) Silencing of microRNAs in vivo with 'antagomirs'. Nature 438:685-9.

Lu, J., Getz, G., Miska, E. A., Alvarez-Saavedra, E., Lamb, J., Peck, D., Sweet-Cordero, A., Ebert, B. L., Mak, R. H., Ferrando, A. A., et al. (2005). MicroRNA expression profiles classify human cancers. Nature 435, 834-838.

Massie, B. M., and Shah, N. B. (1997). Evolving trends in the epidemiologic factors of heart failure: rationale for preventive strategies and comprehensive disease management. Am Heart J 133, 703-712.

Meister, G., Landthaler, M., Peters, L., Chen, P. Y., Urlaub, H., Luhrmann, R., and Tuschl, T. (2005). Identification of Novel Argonaute-Associated Proteins. Curr Biol.

Pfeffer, M. A., and Braunwald, E. (1990). Ventricular remodeling after myocardial infarction. Experimental observations and clinical implications. Circulation 81, 1161-1172.

Smyth G K: Linear models and empirical Bayes methods for assessing differential expression in Microarray experiments. Statistical Applications in Molecular Biology, 2004, Vol. 3, No. 1, Article 3

Thum T, Galuppo P, Wolf C, Fiedler J, Kneitz S, van Laake L W, Doevendans P A, Mummery C L, Borlak J, Haverich A, Gross C, Engelhardt S, Ertl G, Bauersachs J. (2007) MicroRNAs in the human heart: a clue to fetal gene reprogramming in heart failure. Circulation 116:258-67.

Thum T, Borlak J. (2001) Reprogramming of gene expression in cultured cardiomyocytes and in explanted hearts by the myosin ATPase inhibitor butanedione monoxime. Transplantation 71:543-52

Thum T, Fraccarollo D, Galuppo P, Tsikas D, Frantz S, Ertl G, Bauersachs J. (2006) Bone marrow molecular alterations after myocardial infarction: Impact on endothelial progenitor cells. Cardiovasc Res 70:50-60

Zhao, Y., Samal, E., and Srivastava, D. (2005). Serum response factor regulates a muscle-specific microRNA that targets Hand2 during cardiogenesis. Nature 436, 214-220.

The invention claimed is:

1. A method for treating a heart disease comprising inhibiting the expression or activity of SEQ ID NO: 14 in a human subject having heart disease with an oligonucleotide complementary to SEQ ID NO: 14, wherein the heart disease is selected from the group consisting of myocardial infarction, heart failure, chronic heart failure, and cardiac hypertrophy.

2. A method for treating a heart disease in a human subject having an increased expression level of miR-21 in the heart tissue of the subject, comprising inhibiting the expression or activity of SEQ ID NO: 14 in the human subject with an oligonucleotide complementary to SEQ ID NO: 14, wherein the heart disease is selected from the group consisting of myocardial infarction, heart failure, chronic heart failure, and cardiac hypertrophy.

3. The method of claim 1, wherein the heart disease is myocardial infarction.

4. The method of claim 1, wherein the heart disease is heart failure.

5. The method of claim 4, wherein the heart failure is chronic heart failure.

6. The method of claim 1, wherein the heart disease is cardiac hypertrophy.

* * * * *

SEQUENCE LISTING

<160> NUMBER OF SEQ ID NOS: 29

<210> SEQ ID NO 1
<211> LENGTH: 22

```
<212> TYPE: RNA
<213> ORGANISM: Homo sapiens

<400> SEQUENCE: 1
uagcagcaca ucaugguuua ca                                              22

<210> SEQ ID NO 2
<211> LENGTH: 21
<212> TYPE: RNA
<213> ORGANISM: Homo sapiens

<400> SEQUENCE: 2
aucacauugc cagggauuuc c                                               21

<210> SEQ ID NO 3
<211> LENGTH: 21
<212> TYPE: RNA
<213> ORGANISM: Homo sapiens

<400> SEQUENCE: 3
cauuauuacu uuugguacgc g                                               21

<210> SEQ ID NO 4
<211> LENGTH: 22
<212> TYPE: RNA
<213> ORGANISM: Homo sapiens

<400> SEQUENCE: 4
ucacagugaa ccggucucuu uu                                              22

<210> SEQ ID NO 5
<211> LENGTH: 21
<212> TYPE: RNA
<213> ORGANISM: Homo sapiens

<400> SEQUENCE: 5
ugugacuggu ugaccagagg g                                               21

<210> SEQ ID NO 6
<211> LENGTH: 22
<212> TYPE: RNA
<213> ORGANISM: Homo sapiens

<400> SEQUENCE: 6
ucuggcuccg ugucuucacu cc                                              22

<210> SEQ ID NO 7
<211> LENGTH: 22
<212> TYPE: RNA
<213> ORGANISM: Homo sapiens

<400> SEQUENCE: 7
acuagacuga agcuccuuga gg                                              22

<210> SEQ ID NO 8
<211> LENGTH: 22
<212> TYPE: RNA
<213> ORGANISM: Homo sapiens

<400> SEQUENCE: 8
uggaauguaa ggaagugugu gg                                              22

<210> SEQ ID NO 9
```

```
<211> LENGTH: 22
<212> TYPE: RNA
<213> ORGANISM: Homo sapiens

<400> SEQUENCE: 9
uucccuuugu cauccuucgc cu                                              22

<210> SEQ ID NO 10
<211> LENGTH: 21
<212> TYPE: RNA
<213> ORGANISM: Homo sapiens

<400> SEQUENCE: 10
uaacagucuc cagucacggc c                                               21

<210> SEQ ID NO 11
<211> LENGTH: 21
<212> TYPE: RNA
<213> ORGANISM: Homo sapiens

<400> SEQUENCE: 11
acagcaggca cagacaggca g                                               21

<210> SEQ ID NO 12
<211> LENGTH: 22
<212> TYPE: RNA
<213> ORGANISM: Homo sapiens

<400> SEQUENCE: 12
cuggcccucu cugcccuucc gu                                              22

<210> SEQ ID NO 13
<211> LENGTH: 21
<212> TYPE: RNA
<213> ORGANISM: Homo sapiens

<400> SEQUENCE: 13
gugccgccau cuuuugagug u                                               21

<210> SEQ ID NO 14
<211> LENGTH: 22
<212> TYPE: RNA
<213> ORGANISM: Homo sapiens

<400> SEQUENCE: 14
uagcuuauca gacugauguu ga                                              22

<210> SEQ ID NO 15
<211> LENGTH: 23
<212> TYPE: RNA
<213> ORGANISM: Homo sapiens

<400> SEQUENCE: 15
uagcaccauu ugaaaucagu guu                                             23

<210> SEQ ID NO 16
<211> LENGTH: 21
<212> TYPE: RNA
<213> ORGANISM: Homo sapiens

<400> SEQUENCE: 16
cuuuuugcgg ucugggcuug c                                               21
```

```
<210> SEQ ID NO 17
<211> LENGTH: 23
<212> TYPE: RNA
<213> ORGANISM: Homo sapiens

<400> SEQUENCE: 17
aacauucaac gcugucggug agu                                              23

<210> SEQ ID NO 18
<211> LENGTH: 22
<212> TYPE: RNA
<213> ORGANISM: Homo sapiens

<400> SEQUENCE: 18
ugagguagua gguuguaugg uu                                               22

<210> SEQ ID NO 19
<211> LENGTH: 21
<212> TYPE: RNA
<213> ORGANISM: Homo sapiens

<400> SEQUENCE: 19
uaaagugcug acagugcaga u                                                21

<210> SEQ ID NO 20
<211> LENGTH: 22
<212> TYPE: RNA
<213> ORGANISM: Homo sapiens

<400> SEQUENCE: 20
uuuggcaaug guagaacuca ca                                               22

<210> SEQ ID NO 21
<211> LENGTH: 21
<212> TYPE: RNA
<213> ORGANISM: Homo sapiens

<400> SEQUENCE: 21
agggcccccc cucaauccug u                                                21

<210> SEQ ID NO 22
<211> LENGTH: 23
<212> TYPE: RNA
<213> ORGANISM: Homo sapiens

<400> SEQUENCE: 22
uggaguguga caauggyguu ugu                                              23

<210> SEQ ID NO 23
<211> LENGTH: 22
<212> TYPE: RNA
<213> ORGANISM: Homo sapiens

<400> SEQUENCE: 23
uguaaacauc cucgacugga ag                                               22

<210> SEQ ID NO 24
<211> LENGTH: 23
<212> TYPE: RNA
<213> ORGANISM: Homo sapiens

<400> SEQUENCE: 24
cucaaacuau gggggcacuu uuu                                              23
```

```
<210> SEQ ID NO 25
<211> LENGTH: 22
<212> TYPE: RNA
<213> ORGANISM: Homo sapiens

<400> SEQUENCE: 25
uguaaacauc cucgacugga ag                                                  22

<210> SEQ ID NO 26
<211> LENGTH: 21
<212> TYPE: RNA
<213> ORGANISM: Homo sapiens

<400> SEQUENCE: 26
ugauugucca aacgcaauuc u                                                   21

<210> SEQ ID NO 27
<211> LENGTH: 24
<212> TYPE: RNA
<213> ORGANISM: Homo sapiens

<400> SEQUENCE: 27
uucuccaaaa gaaagcacuu ucug                                                24

<210> SEQ ID NO 28
<211> LENGTH: 24
<212> TYPE: RNA
<213> ORGANISM: Homo sapiens

<400> SEQUENCE: 28
cucuugaggg aagcacuuuc uguu                                                24

<210> SEQ ID NO 29
<211> LENGTH: 22
<212> TYPE: RNA
<213> ORGANISM: Homo sapiens

<400> SEQUENCE: 29
uguaaacauc cuacacucag cu                                                  22
```